(12) United States Patent
Chen et al.

(10) Patent No.: US 9,023,318 B2
(45) Date of Patent: May 5, 2015

(54) COMPOUNDS WITH MATRIX-METALLOPROTEINASE INHIBITORY ACTIVITY AND IMAGING AGENTS THEREOF

(71) Applicants: Gang Chen, Rancho Palos Verdes, CA (US); Umesh B. Gangadharmath, Los Angeles, CA (US); Dhanalakshmi Kasi, Los Angeles, CA (US); Harmuth C. Kolb, Playa Del Ray, CA (US); Changhui Liu, Los Angeles, CA (US); Anjana Sinha, San Diego, CA (US); Anna Katrin Szardenings, Torrance, CA (US); Joseph C. Walsh, Pacific Palisades, CA (US); Eric Wang, San Diego, CA (US); Chul Yu, Los Angeles, CA (US); Wei Zhang, Los Angeles, CA (US); Klaus Kopka, Muenster (DE); Guenter Haufe, Muenster (DE); Michael Schaefers, Havixbeck (DE); Verena Hugenberg, Bersenbrueck (DE); Stefan Wagner, Muenster (DE); Sven Hermann, Muenster (DE); Hans-Joerg Breyholz, Muenster (DE); Andreas Faust, Billerbeck (DE)

(72) Inventors: Gang Chen, Rancho Palos Verdes, CA (US); Umesh B. Gangadharmath, Los Angeles, CA (US); Dhanalakshmi Kasi, Los Angeles, CA (US); Harmuth C. Kolb, Playa Del Ray, CA (US); Changhui Liu, Los Angeles, CA (US); Anjana Sinha, San Diego, CA (US); Anna Katrin Szardenings, Torrance, CA (US); Joseph C. Walsh, Pacific Palisades, CA (US); Eric Wang, San Diego, CA (US); Chul Yu, Los Angeles, CA (US); Wei Zhang, Los Angeles, CA (US); Klaus Kopka, Muenster (DE); Guenter Haufe, Muenster (DE); Michael Schaefers, Havixbeck (DE); Verena Hugenberg, Bersenbrueck (DE); Stefan Wagner, Muenster (DE); Sven Hermann, Muenster (DE); Hans-Joerg Breyholz, Muenster (DE); Andreas Faust, Billerbeck (DE)

(73) Assignee: Siemens Medical Solutions USA, Inc., Malvern, PA (US)

(*) Notice: Subject to any disclaimer, the term of this patent is extended or adjusted under 35 U.S.C. 154(b) by 85 days.

(21) Appl. No.: 13/849,646
(22) Filed: Mar. 25, 2013
(65) Prior Publication Data
US 2013/0217887 A1 Aug. 22, 2013

Related U.S. Application Data

(63) Continuation-in-part of application No. 13/155,558, filed on Jun. 8, 2011, now abandoned.
(60) Provisional application No. 61/616,494, filed on Mar. 28, 2012.

(51) Int. Cl.
| | | |
|---|---|---|
| A61K 51/00 | (2006.01) | |
| A61M 36/14 | (2006.01) | |
| C07D 403/14 | (2006.01) | |
| C07D 405/14 | (2006.01) | |
| C07D 249/04 | (2006.01) | |
| C07D 309/12 | (2006.01) | |
| C07D 213/42 | (2006.01) | |

(52) U.S. Cl.
CPC ............ *C07D 403/14* (2013.01); *C07D 405/14* (2013.01); *C07D 249/04* (2013.01); *C07D 309/12* (2013.01); *C07D 213/42* (2013.01)

(58) Field of Classification Search
None
See application file for complete search history.

(56) References Cited

U.S. PATENT DOCUMENTS

| | | |
|---|---|---|
| 5,455,258 A | 10/1995 | Macpherson et al. |
| 6,277,987 B1 | 8/2001 | Kukkola et al. |
| 6,410,580 B1 | 6/2002 | Kukkola et al. |
| 2007/0071670 A1 | 3/2007 | Storey et al. |

FOREIGN PATENT DOCUMENTS

| | | |
|---|---|---|
| WO | 9600214 | 1/1996 |
| WO | 9839329 | 9/1998 |
| WO | 0110827 | 2/2001 |
| WO | 2004069365 | 8/2004 |
| WO | WO 2004069365 A1 * | 8/2004 |
| WO | WO 2005049005 A1 * | 6/2005 |
| WO | WO 2006067376 A2 * | 6/2006 |
| WO | 2007117981 | 10/2007 |
| WO | WO 2008033561 A2 * | 3/2008 |
| WO | 2010007027 | 1/2010 |

OTHER PUBLICATIONS

Faust et al. Bioconjugate Chem. 2008, 19, 1001-1008.*
Hugenberg et al. J. Med. Chem. 2012, 55, 4714-4727.*
Xiong, et al., "The Discovery of a Potent and Selective Lethal Factor Inhibitor for Adjunct Therapy of Anthrax Infection", Bioorganic & Medicinal Chemistry Letters 16 (2006) pp. 964-968.

(Continued)

*Primary Examiner* — Michael G Hartley
*Assistant Examiner* — Sean R Donohue
(74) *Attorney, Agent, or Firm* — Peter Kendall

(57) ABSTRACT

Novel compounds and pharmaceutical compositions having MMP inhibitory activity are disclosed, which have been found to be particularly useful in the prevention, treatment and diagnostic imaging of diseases associated with an unpaired activity of MMP, amongst others MMP-2, MMP-8, MMP-9 and/or MMP-13 to name a few. The compounds of the present invention are useful for the prevention, the treatment and the in vivo diagnostic imaging of a range of disease states (inflammatory, malignant and degenerative diseases) where specific matrix metalloproteinases are known to be involved.

6 Claims, 9 Drawing Sheets

(56) References Cited

OTHER PUBLICATIONS

Faust, et al., "Synthesis and Evaluation of a Novel Hydroxamate Based Fluorescent Photoprobe for Imaging of Matrix Metalloproteinases", Bioconjugate Chem. (2009), 20, pp. 904-912.
International Search Report, PCT/EP2011/062211 dated Oct. 28, 2011.
Wagner, et al., "Novel Fluorinated Derivatives of the Broad-Spectrum MMP Inhibitors N-Hydroxy-2(R)-[[4-methoxyphenyl)sulfonyl] (benzyl)- and (3-picolyl)-amino]-3-methyl-butanamide as Potential Tools for the Molecular Imaging of Activated MMPs with PET", J. Med. Chem. 2007, vol. 50, No. 23, 5752-5764.
European Search Report, EP11165157.6 dated Dec. 16, 2011, 5 pages.

\* cited by examiner

COMPOUNDS WITH MATRIX-METALLOPROTEINASE INHIBITORY ACTIVITY AND IMAGING AGENTS THEREOF

RELATED APPLICATIONS

This application claims priority to provisional patent application U.S. Ser. No. 61/616,494; filed on Mar. 28, 2012; the entire contents of which are incorporated herein by reference. This application is a continuation-in-part application of, and claims priority to, U.S. Ser. No. 13/155,558; filed on Jun. 8, 2011; the entire contents of which are incorporated herein by reference. This application is a continuation-in-part application of, and claims priority to, PCT/EP2011/062211; filed on Jul. 18, 2011; the entire contents of which are incorporated herein by reference.

FIELD OF THE INVENTION

The present invention relates to the field of therapeutic, diagnostic and imaging agents and more specifically to compounds that are inhibitors of matrix-metalloproteinases (MMPs).

BACKGROUND

The matrix-metalloproteinases (MMPs) are a family of at least 20 zinc-dependent endo-peptidases which mediate degradation, or remodeling of the extracellular matrix (ECM). Together, the members of the MMP family can degrade e.g. components of the blood vessel wall and play a major role in both physiological and pathological events that involve the degradation of components of the ECM. Since the MMPs can interfere with the cell-matrix interactions that control cell behavior, their activity affects processes as diverse as cellular differentiation, migration, proliferation and apoptosis. The negative regulatory controls that finely regulate MMP activity in physiological situations do not always function as they should. Inappropriate expression of MMP activity is thought to constitute part of the pathological mechanism in several disease states. MMPs are therefore targets for therapeutic inhibitors in many inflammatory, malignant and degenerative diseases. Consequently, it is believed that synthetic inhibitors of MMPs may be useful in the treatment of many inflammatory, malignant and degenerative diseases. Furthermore, it has been suggested that inhibitors of MMPs may be useful in the diagnosis of these diseases.

The compounds of the present invention are useful for the prevention, the treatment and the in vivo diagnostic imaging of a range of disease states (inflammatory, malignant and degenerative diseases) where specific matrix metalloproteinases are known to be involved. These include: (a) atherosclerosis; (b) CHF; (c) cancer; (d) arthritis; (e) amyotrophic lateral sclerosis; (f) brain metastases; (g) cerebrovascular diseases; (h) Alzheimer's disease; (i) neuroinflammatory diseases; (j) COPD; (k) eye pathology; (l) skin diseases.

SUMMARY

Novel compounds having MMP inhibitory activity are disclosed, which have been found to be particularly useful in the prevention, treatment and diagnostic imaging of diseases associated with an unpaired activity of MMP, amongst others MMP-2, MMP-8, MMP-9 and/or MMP-13 to name a few.

Another aspect of the present invention relates to pharmaceutical compositions useful in prevention, treatment and diagnostic imaging of diseases associated with an unpaired activity of MMP.

The compounds of the present invention are useful for the prevention, the treatment and the in vivo diagnostic imaging of a range of disease states (inflammatory, malignant and degenerative diseases) where specific matrix metalloproteinases are known to be involved.

The compounds of the present invention may be "cold" or comprise "hot" radioactive atoms or molecules. Imaging compounds disclosed herein may have radiolabels selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$.

DETAILED DESCRIPTION

Figure 1B:
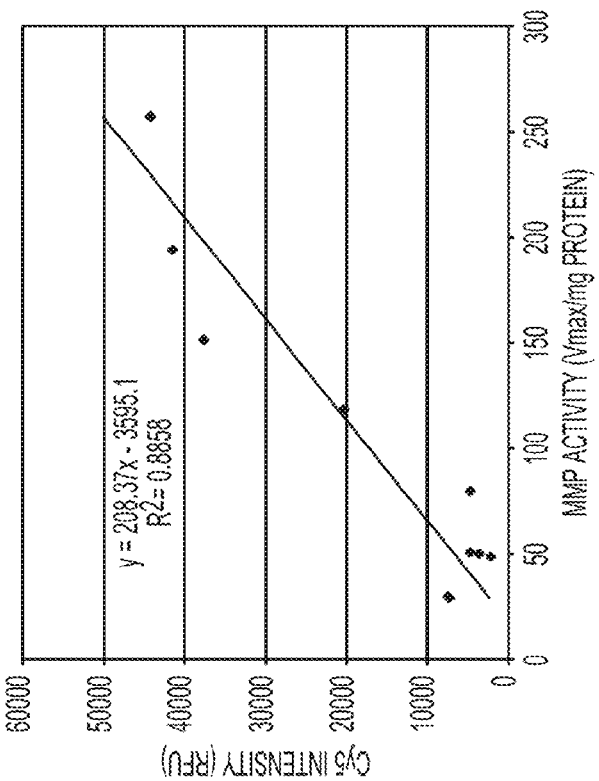
FIG. 1B is a graph showing correlation with fluorescence intensity after M005 injection, 4 h uptake.
Figure 1A:
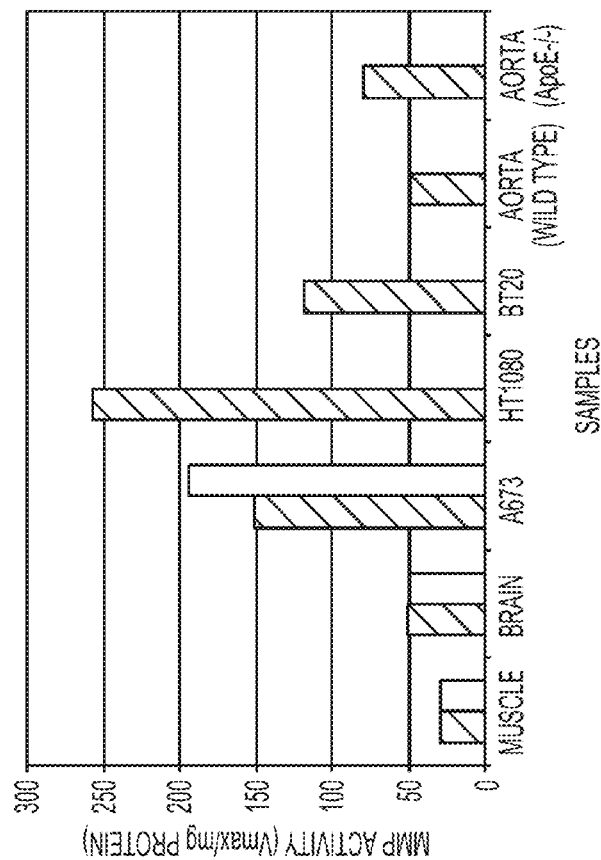
FIG. 1A is a graph showing MMP activity measurement in mouse tumor, muscle, brain and aorta.
Figure 2:
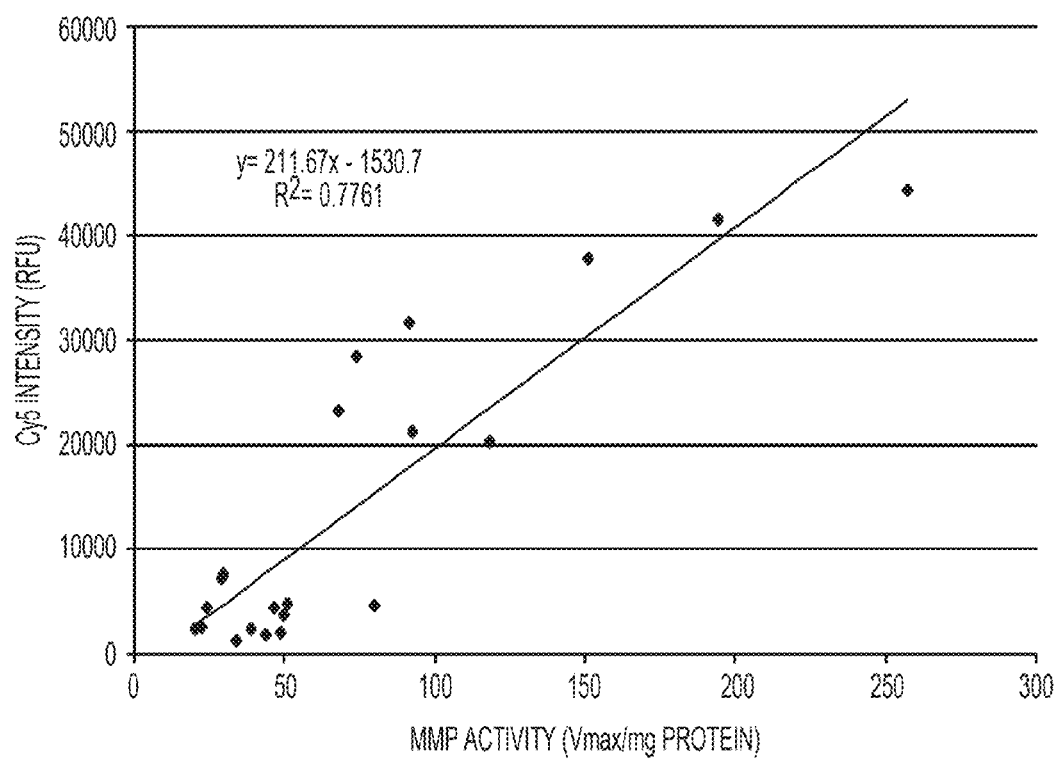
FIG. 2 is a graph showing correlation with fluorescence intensity after M005 injection, 4 h uptake (all experiments)
Figure 3:
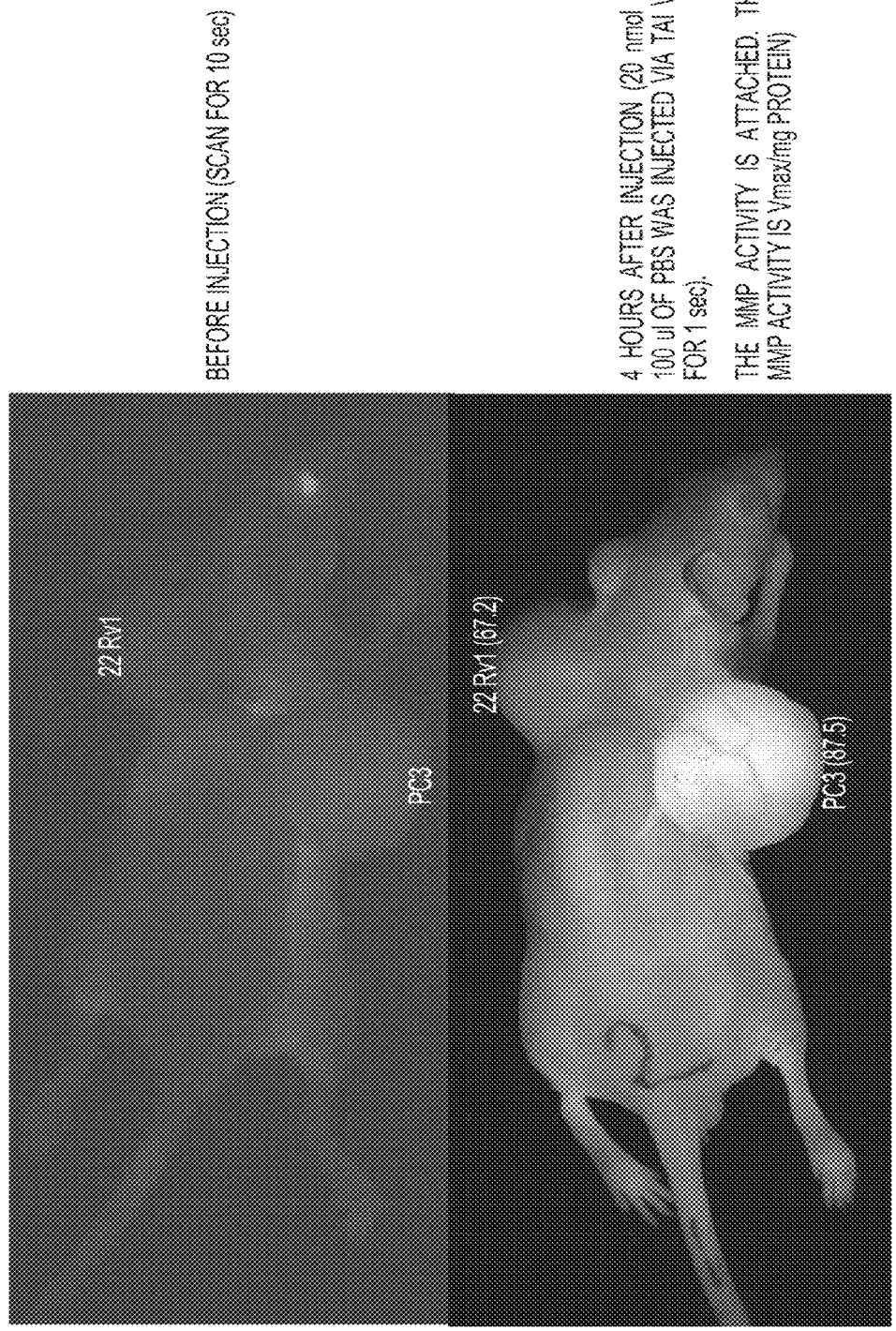
FIGS. 3-5 are mouse scans before and 4 hours after M005 injection.
Figure 4:
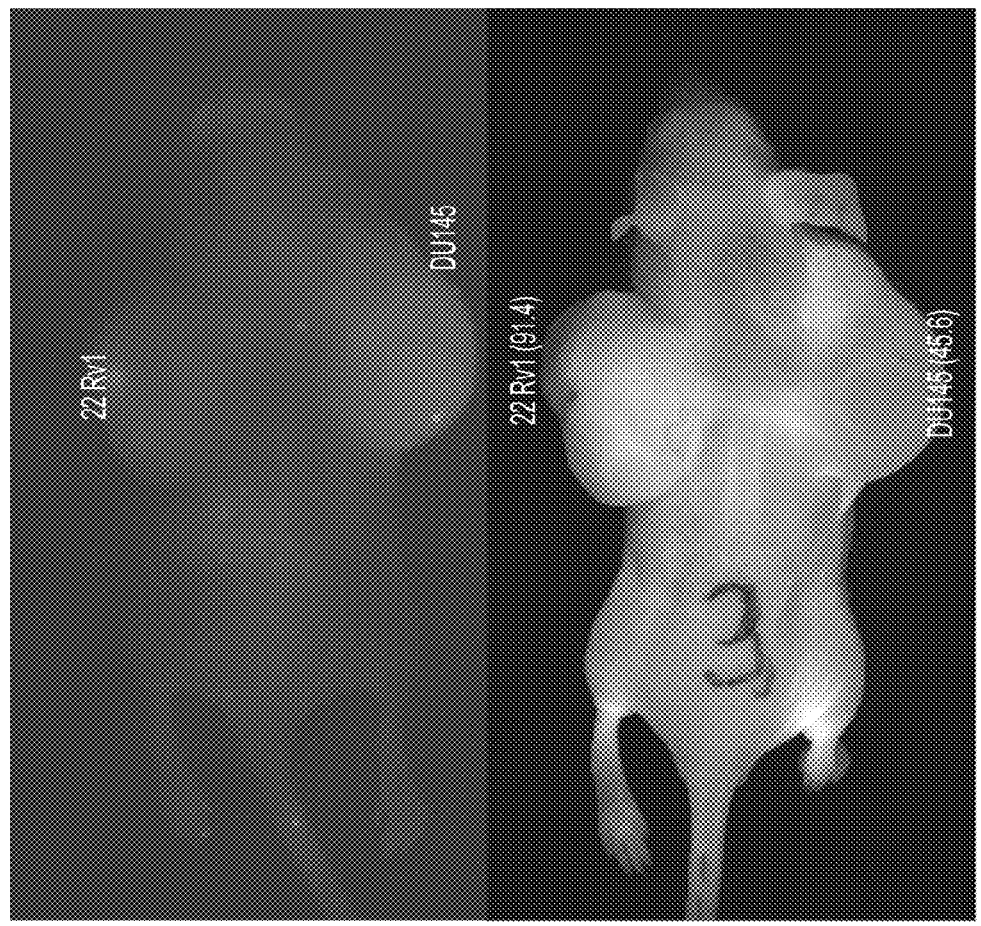
Figure 5:
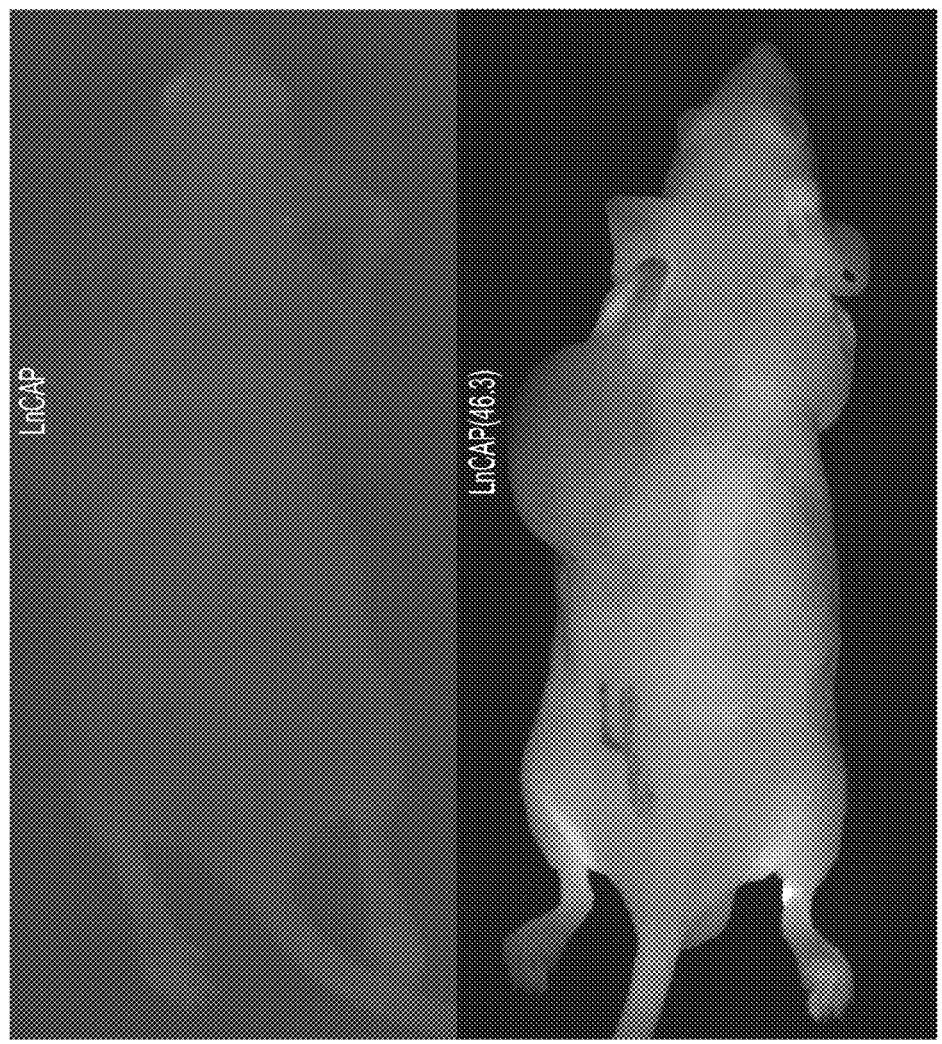

The compounds of the invention may be used as therapeutics and/or in vivo diagnostic agents. In a further aspect, the present compounds may be used to prevent and/or treat pathological conditions associated with unpaired expression of matrix-metalloproteases in human and animal, in particular mammals.

In another aspect, the present invention relates to compounds that are labeled with a radionuclide such as an $^{18}F$ atom for use as a diagnostic or imaging agent, in particular as an in vivo diagnostic or imaging agent and more in particular as diagnostic or imaging agent for Positron Emission Tomography (PET) or SPECT.

The compounds may be used to visualize, assess and quantify MMP-activity in cells and tissues. Preferably, molecular imaging agents are for visualizing and quantifying MMP-activity in mammalian cells and tissues, including human cells and tissues. This may comprise analyzing cellular or tissue radioactivity content, or the rate of uptake, displacement, dissociation or partitioning.

The compounds of the invention may be used in the prevention or treatment of pathological conditions associated with a dysregulated expression of matrix metalloproteinase in human and animal.

The radiolabeled compounds of the invention may be used for diagnosing pathological conditions associated with a dysregulated expression of matrix metalloproteinase in human and animal.

The pathological condition may be selected from the group consisting of cardiovascular diseases, inflammatory diseases, autoimmune diseases and malignant diseases. In particular the cardiovascular diseases may be selected from atherosclerosis and congestive heart failure. Inflammatory disease is chronic obstructive pulmonary disease. Autoimmune diseases are diabetes mellitus type 1, rheumatoid arthritis, multiple sclerosis, and malignant diseases are cancers.

The diagnostic imaging compound of the invention permits the identification of active plaque burden, which allows risk stratification of patients with known or suspected coronary artery disease, i.e. patients with pain or a history of pain, or identified as high risk but asymptomatic.

In addition, the diagnostic imaging agents of the invention permit identification of vulnerable plaques in symptomatic patients, which may allow identification of high risk of acute myocardial infarction or stroke irrespective of stenosis and permits immediate risk stratification when the patient suffers from chest pain Furthermore, angioplasty of vulnerable plaques is high risk, and may lead to embolism of the artery tree post surgery. Thus imaging of this subtype of plaques may help reduce post-surgical complication.

Suitable preparations include for example tablets, capsules, suppositories, solutions, —particularly solutions for injection (s.c, i.v., i.m.) and infusion—syrups, elixirs, solution for inhalation.

The invention relates to pharmaceutical compositions comprising an effective amount, especially an amount effective in the treatment of one of the above-mentioned disorders, of the active ingredient together with pharmaceutically acceptable carriers that are suitable for topical, enteral, for example oral or rectal, or intravenous or parenteral administration and that may be inorganic or organic, solid or liquid. They are used for oral administration especially tablets or gelatin capsules that comprise the active ingredient together with diluents, for example lactose, dextrose, sucrose, mannitol, sorbitol, cellulose and/or glycerol, and/or lubricants, for example silica, talc, stearic acid or salts thereof, such as magnesium or calcium stearate and/or polyethylene glycol. Tablets may also comprise binders, for example magnesium aluminum silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate and/or effervescent mixtures or adsorbents, dyes, flavorings and sweeteners.

It is also possible to use the pharmacologically active compounds of the present invention in the form of intravenously and parentally administrable compositions or in the form of infusion solutions. Such solutions are preferably isotonic aqueous solutions or suspensions which, for example in the case of lyophilized compositions that comprise the active ingredient alone or together with a carrier, for example mannitol, can be made up prior to use. The pharmaceutical compositions may be sterilized and/or may comprise excipients, for example preservatives, stabilizers, wetting agents and/or emulsifiers, solubilizes, salts for regulating the osmotic pressure and/or buffers. The present pharmaceutical compositions are prepared in a manner known per se, for example by means of conventional mixing, granulating, confectioning, dissolving or lyophilizing processes, and comprise approximately from 1% to 95%, especially from approximately 1% to approximately 20%, active ingredient (s).

In one embodiment, the invention is a compound of the formula:

and pharmaceutically acceptable salts and stereoisomers thereof, wherein:

$R_1$ is selected from the group consisting of: $C_{1-6}$alkyl, $C_{1-6}$alkyl-halo, protecting group or leaving group;

A is a bond or is $(CH_2)_{1-5}$;

$R_3$ is selected from the group consisting of: OH, $NH_2$, protecting group or leaving group;

$R_4$ is a bond or is at least one selected from the group consisting of: aryl, heteroaryl, $C_{1-20}$alkyl, wherein at least one C of $C_{1-20}$alkyl is optionally replaced by O, S, NH, C(O), aryl or heteroaryl and wherein at least one H of $C_{1-20}$alkyl is optionally replaced with OH, $NH_2$, COOH, wherein at least one C of $C_{1-8}$alkyl is optionally replaced by O, S, C(O), aryl, heteroaryl or NH, $R_5$ is selected from the group consisting of: H, halo, $CH_3$, $NH_2$, OH, $SO_2$, $NO_2$, —O—$C_{1-6}$alkyl and wherein at least one H or halo is optionally replaced with a radionuclide.

In one embodiment, A is a bond.
In one embodiment, $R_1$ is $C_{1-6}$alkyl.
In one embodiment, $R_3$ is OH.
In one embodiment, $R_5$ is a halo or a radionuclide.
In one embodiment, $R_4$ is $C_{1-20}$alkyl, wherein at least one C of $C_{1-20}$alkyl is optionally replaced by O, S, NH, C(O).
In one embodiment, $R_4$ is aryl.
In one embodiment, $R_4$ is:

In one embodiment, $R_4$ is $C_{1-20}$alkyl, wherein: at least one C of $C_{1-20}$alkyl is replaced by O, at least one C of $C_{1-20}$alkyl is replaced by C(O)NH, at least one C of $C_{1-20}$alkyl is replaced by aryl, at least one C of $C_{1-20}$alkyl is replaced by heteroaryl, wherein at least one H of the aryl is replaced by COOH.

In one embodiment, $R_4$ is —[$(CH_2)_2$—O]$_{1-6}$—.

In one embodiment, $R_5$ is:

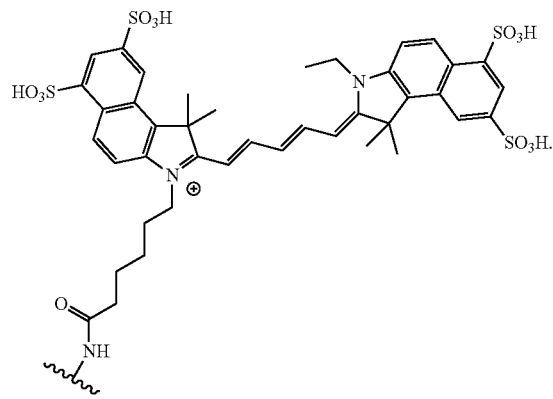 [SMILES: *NC(=O)CCCCC[N+]1=C(/C=C/C=C/C=C2\N(CC)c3ccc4c(S(=O)(=O)O)cc(S(=O)(=O)O)cc4c3C2(C)C)C(C)(C)c2c1ccc1c(S(=O)(=O)O)cc(S(=O)(=O)O)cc21]

In one embodiment, the heteroaryl is a triazole.

In one embodiment, at least one H of $C_{1-20}$ alkyl is replaced with

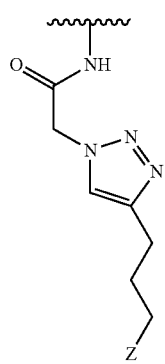

wherein Z is a halo or a radionuclide.

In one embodiment, $R_4$ is

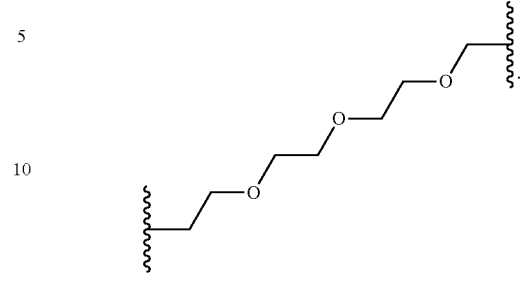

In one embodiment, the invention is a compound of:

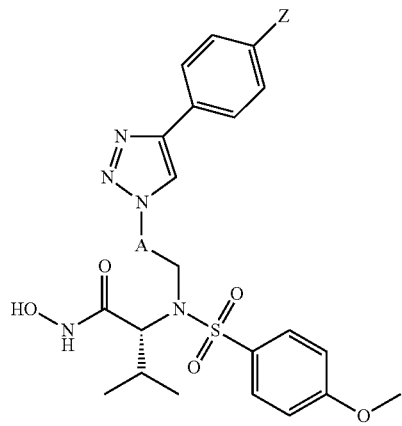

wherein Z is selected from the group consisting of: $NH_2$, OMe, halo or radionuclide.

In one embodiment, the invention is a compound of:

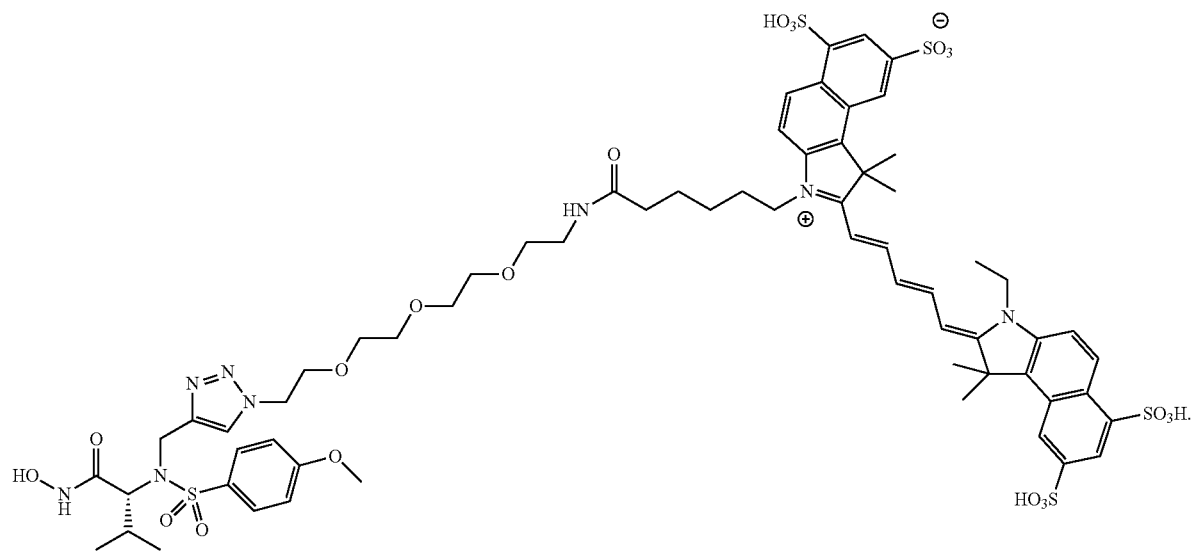

In one embodiment, the invention is a compound of:

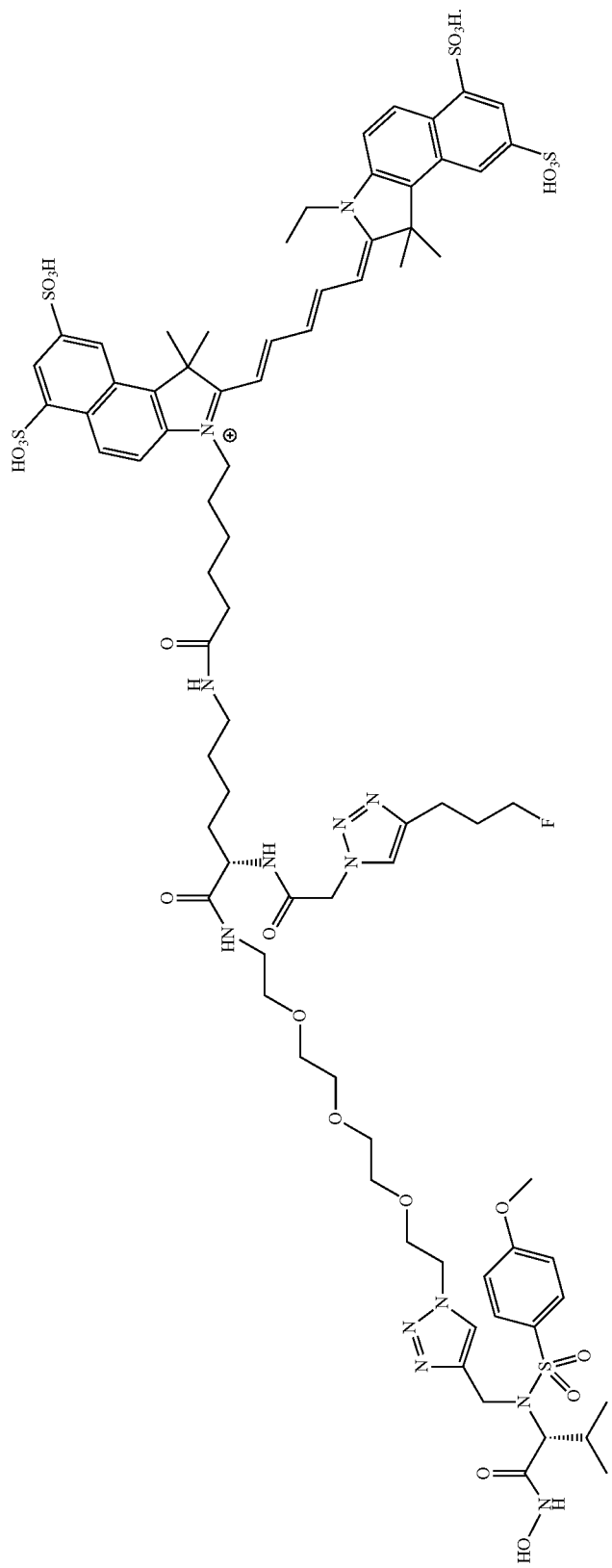

In one embodiment, the invention is a compound of:

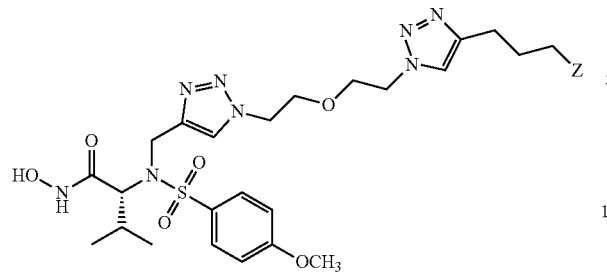

wherein Z is a halo or a radionuclide.
In one embodiment, the invention is a compound of:

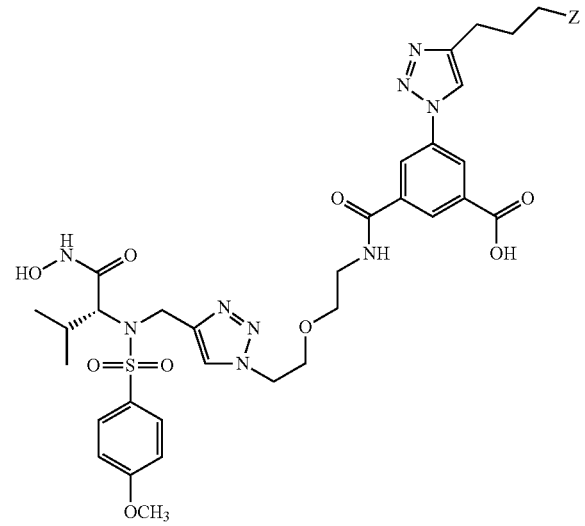

wherein Z is a halo or a radionuclide.
In one embodiment, the invention is a compound that is:

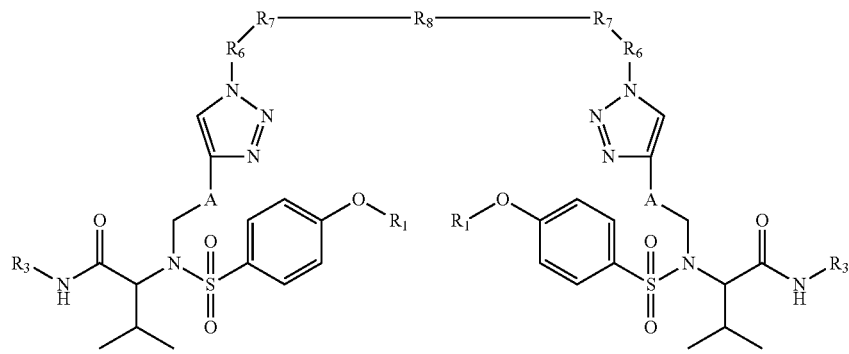

and pharmaceutically acceptable salts and stereoisomers thereof,
wherein:
each $R_1$ is independently selected from the group consisting of: $C_{1-6}$alkyl, $C_{1-6}$alkyl-halo, protecting group or leaving group;
each A is independently a bond or is $(CH_2)_{1-5}$;
each $R_3$ is independently selected from the group consisting of: OH, $NH_2$, protecting group or leaving group;
each $R_6$ is independently a bond or is at least one selected from the group consisting of: aryl, heteroaryl, or
$C_{1-20}$alkyl, wherein at least one C of $C_{1-20}$alkyl is optionally replaced by O, S, NH, C(O), aryl or heteroaryl and wherein at least one H of $C_{1-20}$alkyl is optionally replaced with OH, $NH_2$, $C_{1-8}$alkyl, $C_{1-8}$alkyl-halo, wherein at least one C of $C_{1-8}$alkyl is optionally replaced with at least one of O, S, C(O), NH, aryl and heteroaryl;
each $R_7$ is independently a bond or is at least one selected from the group consisting of: $CH_2$, NH, C(O)NH, $C_{1-6}$alkyl, wherein at least one C of $C_{1-6}$alkyl is optionally replaced by O, S, NH, C(O) and wherein at least one H of $C_{1-6}$alkyl is optionally replaced by OH, $NH_2$, $SO_2$, $C_{1-8}$alkyl, $C_{1-8}$alkyl-halo,
wherein at least one C of $C_{1-8}$alkyl is optionally replaced by O, S, C(O), aryl, heteroaryl or NH,
$R_8$ is a bond or is at least one selected from the group consisting of: O, NH, S, aryl, heteroaryl, wherein at least one H of aryl or heteroaryl is optionally replaced with $C_{1-8}$alkyl, $C_{1-8}$alkyl-halo,
wherein at least one C of $C_{1-8}$alkyl is optionally replaced with at least one of O, S, C(O), NH, aryl and heteroaryl;
$(CH_2)_{1-6}$, wherein at least one C of $(CH_2)_{1-6}$ is optionally replaced by O, NH or S;
wherein at least one H or halo is optionally replaced with a radionuclide.

In one embodiment, each A is a bond.
In one embodiment, each $R_3$ is OH.
In one embodiment, each $R_1$ is $CH_3$.
In one embodiment, each $R_6$ is a bond.
In one embodiment, $R_8$ is O.
In one embodiment, each $R_7$ is $C_{1-6}$alkyl.
In one embodiment, each $R_6$ is $C_{1-20}$alkyl, wherein at least one C of $C_{1-20}$alkyl is optionally replaced by O, S, NH, C(O), aryl or heteroaryl and wherein at least one H of $C_{1-20}$alkyl is optionally replaced with OH, $NH_2$, $C_{1-8}$alkyl, $C_{1-8}$alkyl-halo, wherein at least one C of $C_{1-8}$alkyl is optionally replaced with at least one of O, S, C(O), NH, aryl and heteroaryl.

In one embodiment, each $R_6$ is —[$(CH_2)_2$—O]$_{1-6}$—.

In one embodiment, each $R_6$ is:

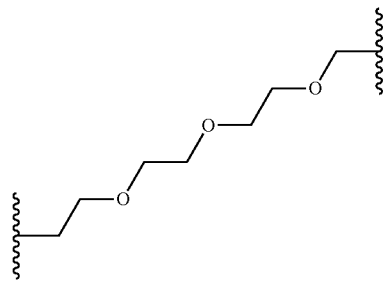 [SMILES: *CCOCCOCCOC*]

In one embodiment, each $R_7$ is $C_{1-6}$alkyl, wherein at least one C of $C_{1-6}$alkyl is optionally replaced by O, S, NH, C(O) and at least one H is replaced with:

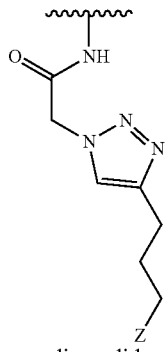

wherein Z is a halo or a radionuclide.

In one embodiment, each $R_7$ is $CH_2C(O)NH$.

In one embodiment, $R_8$ is aryl.

In one embodiment, at least one H of aryl is replaced with $C_{1-8}$alkyl-halo, wherein at least one C of $C_{1-8}$alkyl-halo is optionally replaced with heteroaryl.

In one embodiment, the invention is a compound that is:

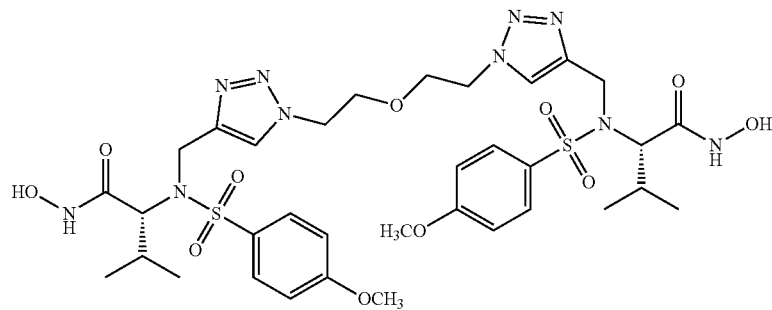 [SMILES: COc1ccc(S(=O)(=O)N(Cc2cn(CCOCCn3cc(CN([C@@H](C(=O)NO)C(C)C)S(=O)(=O)c4ccc(OC)cc4)nn3)nn2)[C@H](C(=O)NO)C(C)C)cc1]

and pharmaceutically acceptable salts and stereoisomers thereof.

In one embodiment, the invention is compound that is:

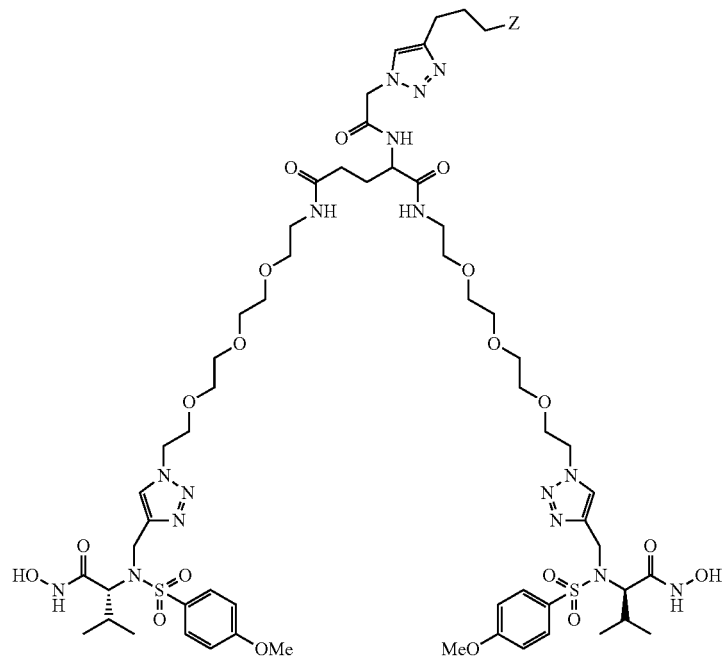

and pharmaceutically acceptable salts and stereoisomers thereof,
wherein Z is a halo or a radionuclide.

In one embodiment, the invention is compound that is:

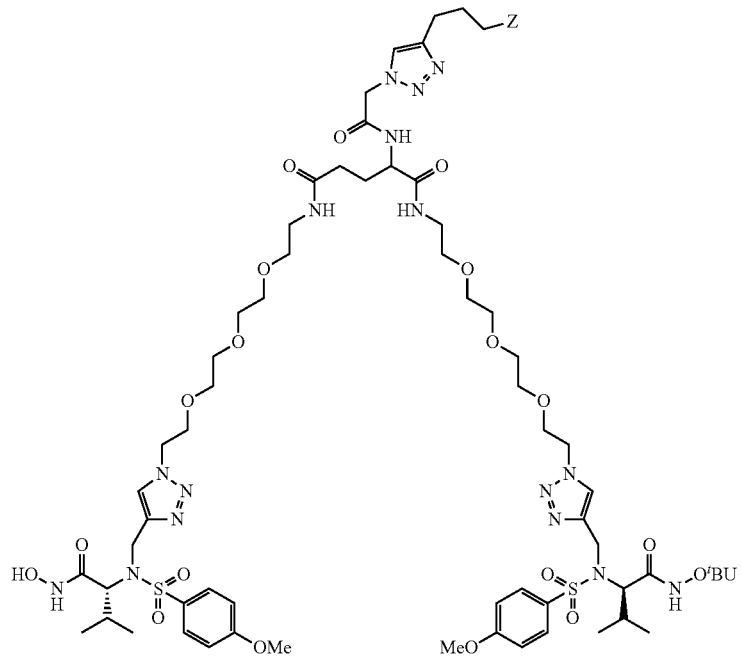

and pharmaceutically acceptable salts and stereoisomers thereof,
wherein Z is a halo or a radionuclide.

In one embodiment, the invention is compound that is:

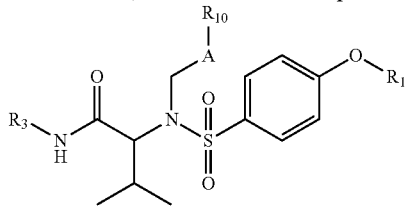

and pharmaceutically acceptable salts and stereoisomers thereof,
wherein:
$R_1$ is selected from the group consisting of: $C_{1-6}$alkyl, $C_{1-6}$alkyl-halo, protecting group or leaving group;
A is a bond or is $(CH_2)_{1-5}$;
$R_3$ is selected from the group consisting of: OH, NH$_2$, protecting group or leaving group;
$R_{10}$ is selected from the group consisting of: an alkyne, an azide, $C_1$-$C_6$-alkyne, $C_1$-$C_6$-azide, wherein at least one C is optionally replaced by NH, C(O), S or O.

In one embodiment, the invention is compound that is:

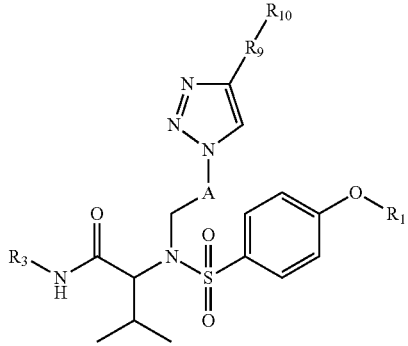

and pharmaceutically acceptable salts and stereoisomers thereof,
wherein:
$R_1$ is selected from the group consisting of: $C_{1-6}$alkyl, $C_{1-6}$alkyl-halo, protecting group or leaving group;
A is a bond or is $(CH_2)_{1-5}$;
$R_3$ is selected from the group consisting of: OH, NH$_2$, protecting group or leaving group;
$R_9$ is a bond or is at least one selected from the group consisting of: aryl, heteroaryl,
  $C_{1-20}$alkyl, wherein at least one C of $C_{1-20}$alkyl is optionally replaced by O, S, NH, C(O), aryl or heteroaryl and wherein at least one H of $C_{1-20}$alkyl is optionally replaced with OH, NH$_2$, COOH, $C_{1-8}$alkyl, $C_{1-8}$alkyl-halo,
  wherein at least one C of $C_{1-8}$alkyl is optionally replaced by O, S, C(O), aryl, heteroaryl or NH,
$R_{10}$ is selected from the group consisting of: an alkyne, an azide, $C_1$-$C_6$-alkyne, $C_1$-$C_6$-azide, wherein at least one C is optionally replaced by NH, C(O), S or O.

In one embodiment, the invention is compound that is:

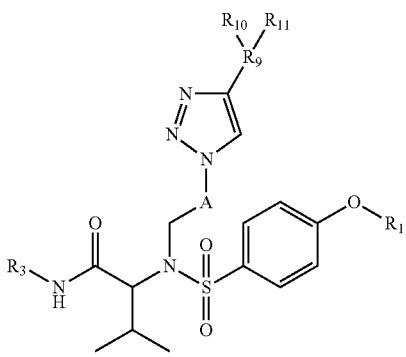

and pharmaceutically acceptable salts and stereoisomers thereof,
wherein:
$R_1$ is selected from the group consisting of: $C_{1-6}$alkyl, $C_{1-6}$alkyl-halo, protecting group or leaving group;
A is a bond or is $(CH_2)_{1-5}$;

$R_3$ is selected from the group consisting of: OH, $NH_2$, protecting group or leaving group;

$R_9$ is a bond or is at least one selected from the group consisting of: aryl, heteroaryl, $C_{1-20}$alkyl, wherein at least one C of $C_{1-20}$alkyl is optionally replaced by O, S, NH, C(O), aryl or heteroaryl and wherein one H of $C_{1-20}$alkyl is optionally replaced with OH, $NH_2$, COOH, $C_{1-8}$alkyl, $C_{1-8}$alkyl-halo, wherein at least one C of $C_{1-8}$alkyl is optionally replaced by O, S, C(O), aryl, heteroaryl or NH, $R_{10}$ is selected from the group consisting of: an alkyne, an azide, $C_1$-$C_6$-alkyne, $C_1$-$C_6$-azide, wherein at least one C of $C_1$-$C_6$ is optionally replaced by NH, C(O), S or O;

$R_{11}$ is selected from the group consisting of: H, $CH_3$, $NH_2$, OH, $SO_2$, $NO_2$, —O—$C_{1-6}$alkyl and

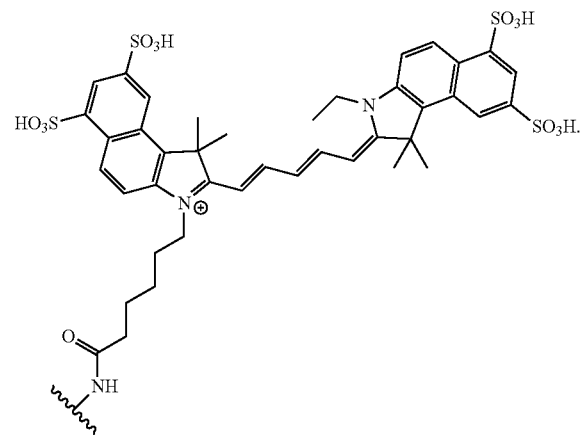 [SMILES: *NC(=O)CCCCC[N+]1=C(/C=C/C=C/C=C2\N(CC)c3ccc4c(S(=O)(=O)O)cc(S(=O)(=O)O)cc4c3C2(C)C)C(C)(C)c2c1ccc1c(S(=O)(=O)O)cc(S(=O)(=O)O)cc21]

In one embodiment, the invention is compound that is:

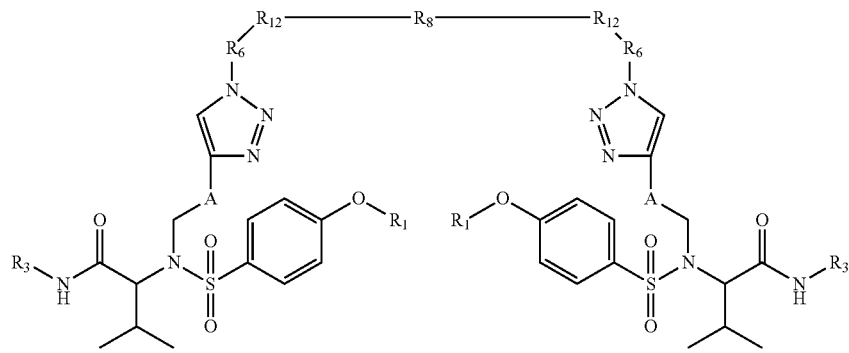

and pharmaceutically acceptable salts and stereoisomers thereof, wherein:

each $R_1$ is independently selected from the group consisting of: $C_{1-6}$alkyl, $C_{1-6}$alkyl-halo, protecting group or leaving group;

each A is independently a bond or is $(CH_2)_{1-5}$;

each $R_3$ is independently selected from the group consisting of: OH, $NH_2$, protecting group or leaving group;

each $R_6$ is independently a bond or is at least one selected from the group consisting of: aryl, heteroaryl, or $C_{1-20}$alkyl, wherein at least one C of $C_{1-20}$alkyl is optionally replaced by O, S, NH, C(O), aryl or heteroaryl and wherein at least one H of $C_{1-20}$alkyl is optionally replaced with OH, $NH_2$, $C_{1-8}$alkyl, $C_{1-8}$alkyl-halo, wherein at least one C of $C_{1-8}$alkyl is optionally replaced with at least one of O, S, C(O), NH, aryl and heteroaryl;

each $R_{12}$ is independently a bond or is $C_{1-6}$alkyl, wherein at least one C of $C_{1-6}$alkyl is optionally replaced by O, S, NH, C(O) and wherein at least one H of $C_{1-6}$alkyl is optionally replaced by OH, $NH_2$, $SO_2$, $C_{1-8}$alkyl, $C_{1-8}$alkyl-halo, azide or alkyne, wherein at least one C of $C_{1-8}$alkyl is optionally replaced by O, S, C(O), aryl, heteroaryl or NH, $R_8$ is a bond or is at least one selected from the group consisting of: O, NH, S, aryl, heteroaryl, wherein at least one H of aryl or heteroaryl is optionally replaced with $C_{1-8}$alkyl, $C_{1-8}$alkyl-halo, wherein at least one C of $C_{1-8}$alkyl is optionally replaced with at least one of O, S, C(O), NH, aryl and heteroaryl;

$(CH_2)_{1-6}$, wherein at least one C of $(CH_2)_{1-6}$ is optionally replaced by O, NH or S.

In a further aspect the present invention therefore provides a method for the molecular imaging of MMP-activity which comprises the steps of:

a. contacting said cells or tissues with a radiolabeled compound of the present invention or composition of the present invention and b. detecting said MMP-activity.

Preferably, the step of detecting said MMP-activity comprises the steps of positioning the subject within the detection field of a detection device and detecting said compounds in the subject with said detection device.

This method may be carried out also in vitro by contacting the cells or tissues with a compound or composition of the present invention by exposing, incubating, touching, associating or making the compound accessible to the cells or tissue. When the compound or composition of the present invention is radiolabeled, said MMP-activity can be detected in vitro, ex vivo and in vivo using any appropriate radiation detection device.

The compounds or compositions may be administered to a subject by any suitable administration method (oral, injection (intravenous (IV), intramuscular (IM), and subcutaneous, parenteral), via inhalation, etc.). Preferably, the compounds are administered intravenously.

When the compound or composition of the present invention is radiolabeled, said MMP-activity may be detected using a radiation detection device. Said radiation detection device may include a Positron Emission Tomography (PET) scanner or a Single Photon Emission Computed Tomography (SPECT) scanner. Preferably, said radiation detection device is a Positron Emission Tomography (PET) scanner combined with Computer Tomography (PET/CT) or Magnetic Resonance Tomography (PET/MR). Said PET scanner can detect pairs of gamma rays, emitted indirectly by positron-emitting radioisotopes such as $^{18}F$ to produce a reconstructed 3D image of the radioactivity distribution within tissues. PET can therefore be used to produce a 3D image of the distribution of the radiolabeled compounds and compositions of the present invention within mammalian or human tissues.

| ID | Structure | MW | cLogP | MMP-2 IC50, nM | MMP-8 IC50, nM | MMP-9 IC50, nM | MMP-13 IC50, nM |
|---|---|---|---|---|---|---|---|
| M001 | 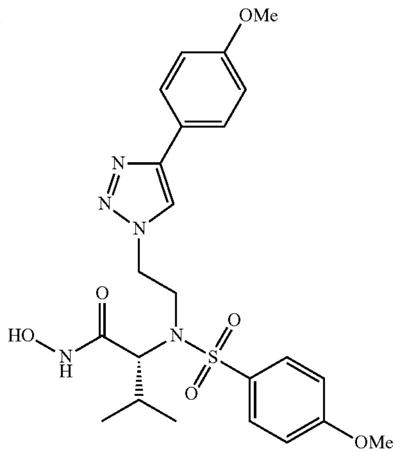 [SMILES: COc1ccc(-c2cn(CCN([C@@H](C(=O)NO)C(C)C)S(=O)(=O)c3ccc(OC)cc3)nn2)cc1] | 504 | 3.2 | | 92% 100 nM | | 99% 100 nM |
| M002 | 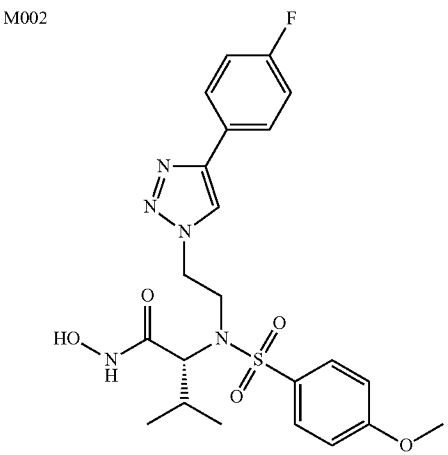 | 492 | 3.4 | | | | |

-continued
| ID | Structure | MW | cLogP | MMP-2 IC50, nM | MMP-8 IC50, nM | MMP-9 IC50, nM | MMP-13 IC50, nM |
|---|---|---|---|---|---|---|---|
| M003 | 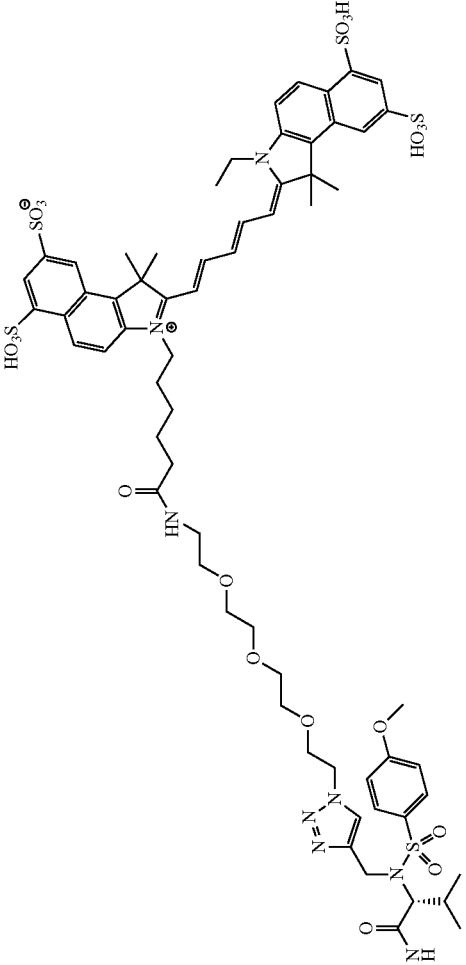 | 1458 | | 5.2 | 97% 100 nM | | 97% 100 nM |
| M004 | 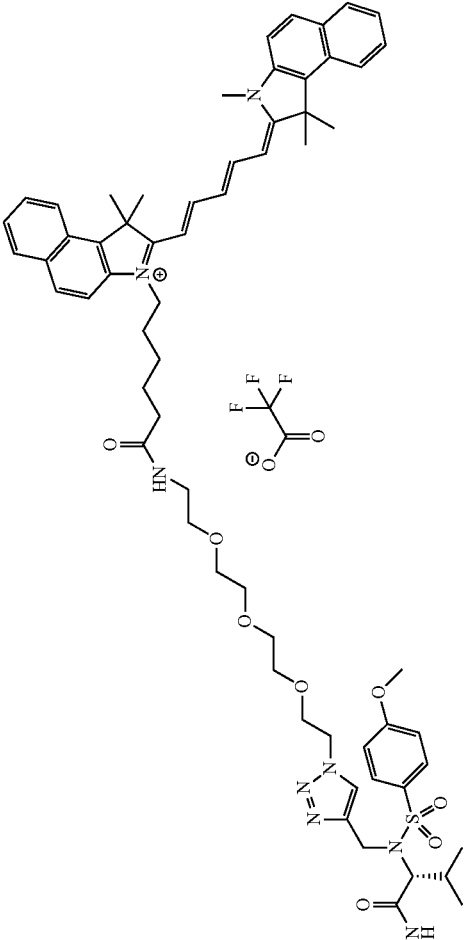 | 1237 | | 25 | 83% 100 nM | | 91% 100 nM |

-continued

| ID | Structure | MW | cLogP | MMP-2 IC50, nM | MMP-8 IC50, nM | MMP-9 IC50, nM | MMP-13 IC50, nM |
|---|---|---|---|---|---|---|---|
| M005 | 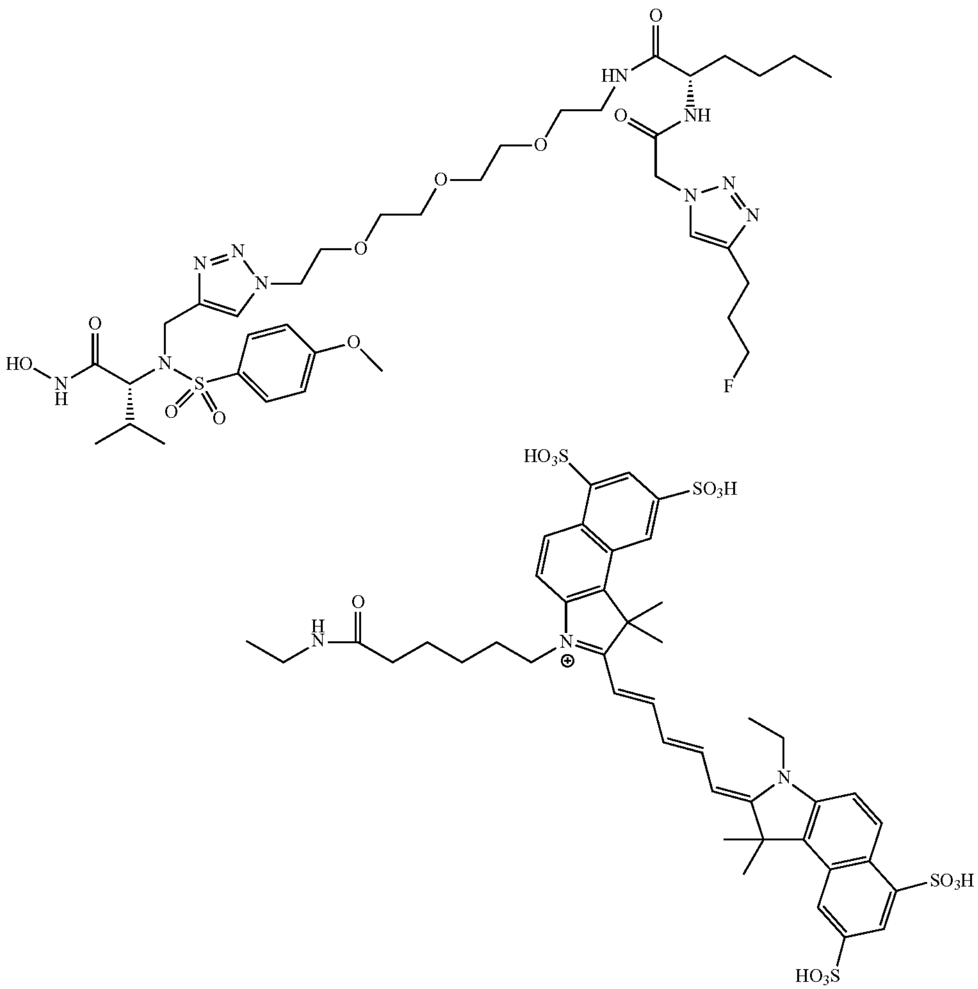 | 1756 | | 2 | 97% (100 nM) | 2.1 | 100% 100 nM |

-continued

| ID | Structure | MW | cLogP | MMP-2 IC50, nM | MMP-8 IC50, nM | MMP-9 IC50, nM | MMP-13 IC50, nM |
|---|---|---|---|---|---|---|---|
| Cy5.5 | (structure shown) | 917 | | 0% (1 uM)<br>0% (0.1 uM) | 1% (1 uM)<br>0% (0.1 uM) | 17% (1 uM)<br>12% (0.1 uM) | 7% at 1 uM,<br>0% at 0.1 uM |
| M006 | (structure shown) | 475 | | | | | |
| M007 | (structure shown) | 837 | | 64% (10 nM)<br>95%(100 nM) | 94% (10 nM)<br>100% (100 nM) | 89% (10 nM)<br>100% (100 nM) | 96% (10 nM)<br>99% (100 nM) |

-continued

| ID | Structure | MW | cLogP | MMP-2 IC50, nM | MMP-8 IC50, nM | MMP-9 IC50, nM | MMP-13 IC50, nM |
|---|---|---|---|---|---|---|---|
| M008 | 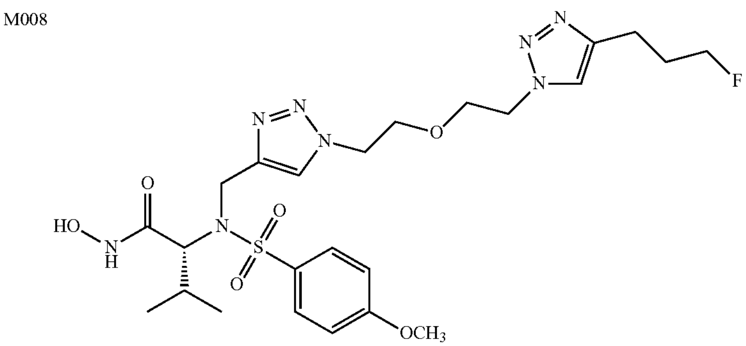 | 583 | | 82% (10 nM) | 95% (10 nM) | 78% (10 nM) | 82% (10 nM) |
| M009 | 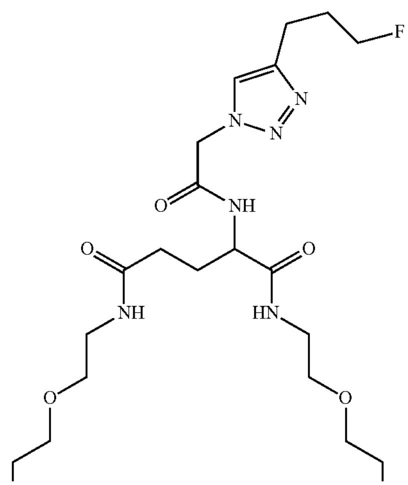 | 1398 | | 59% (10 nM) | 46% (10 nM) | 48% | 64% (10 nM) |

-continued

| ID | Structure | MW | cLogP | MMP-2 IC50, nM | MMP-8 IC50, nM | MMP-9 IC50, nM | MMP-13 IC50, nM |
|---|---|---|---|---|---|---|---|
| M010 | 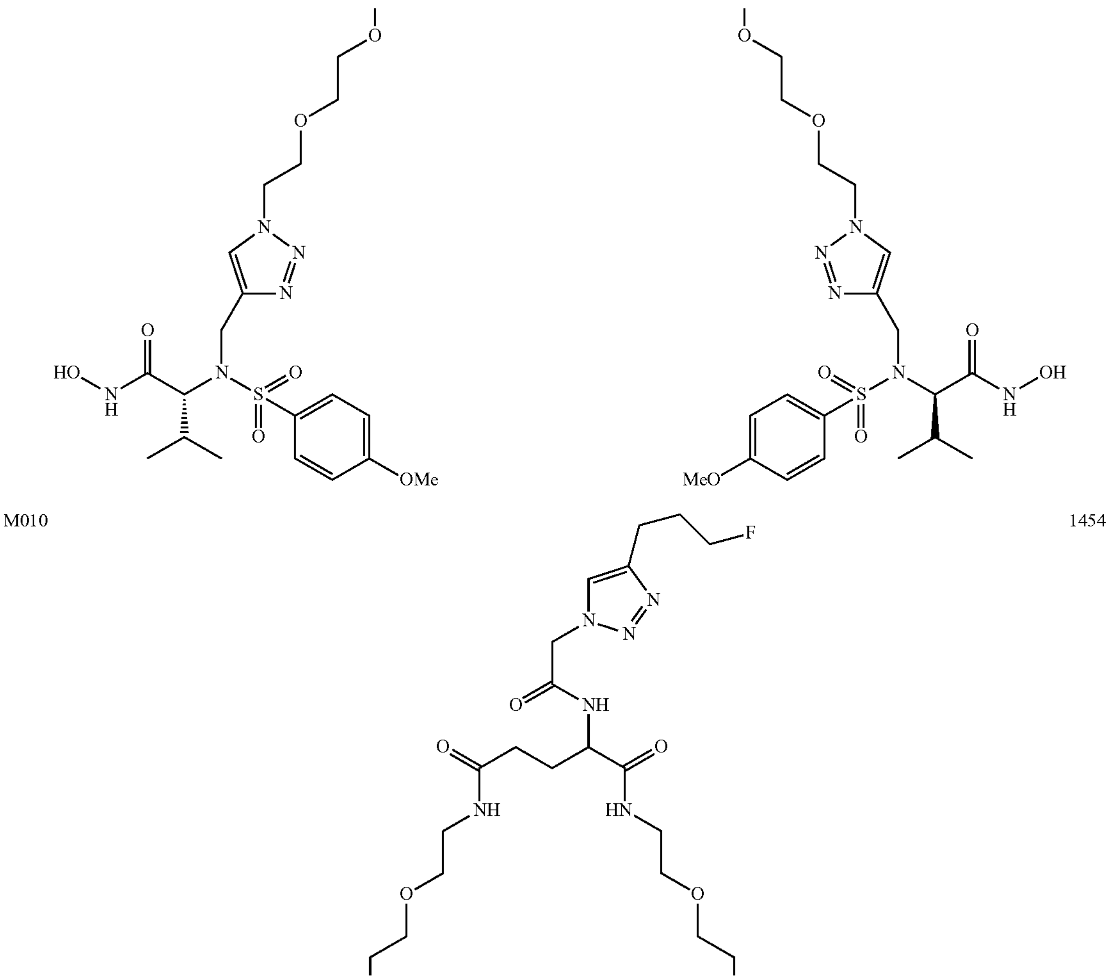 | 1454 | | 28% (10 nM) | 13% (10 nM) | 2% (10 nM) | 10% (10 nM) |

| ID | Structure | MW | cLogP | MMP-2 IC50, nM | MMP-8 IC50, nM | MMP-9 IC50, nM | MMP-13 IC50, nM |
|---|---|---|---|---|---|---|---|
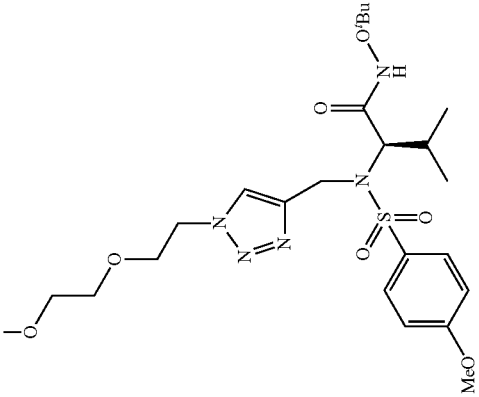
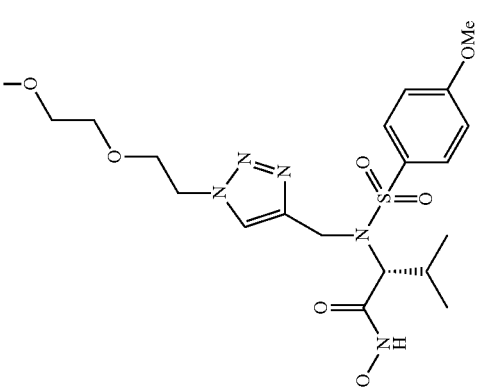

-continued
| ID | Structure | MW | cLogP | MMP-2 IC50, nM | MMP-8 IC50, nM | MMP-9 IC50, nM | MMP-13 IC50, nM |
|---|---|---|---|---|---|---|---|
| M011 | 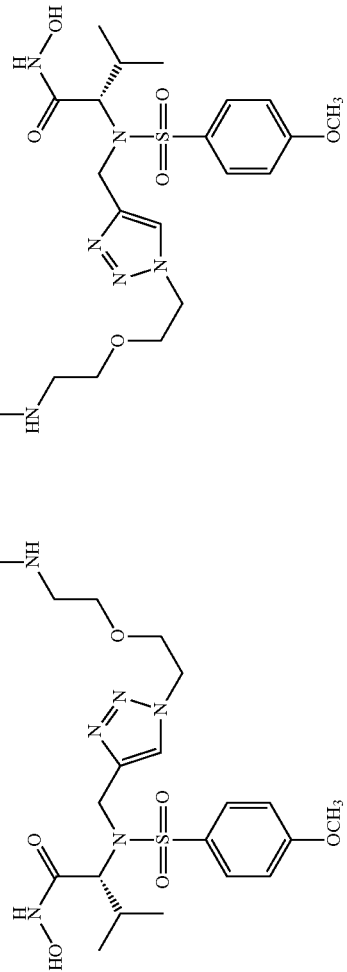 | 1198 | | 50% (10 nM) | 57% (10 nM) | 55% (10 nM) | 75% (10 nM) |

-continued
| ID | Structure | MW | cLogP | MMP-2 IC50, nM | MMP-8 IC50, nM | MMP-9 IC50, nM | MMP-13 IC50, nM |
|---|---|---|---|---|---|---|---|
| M012 | 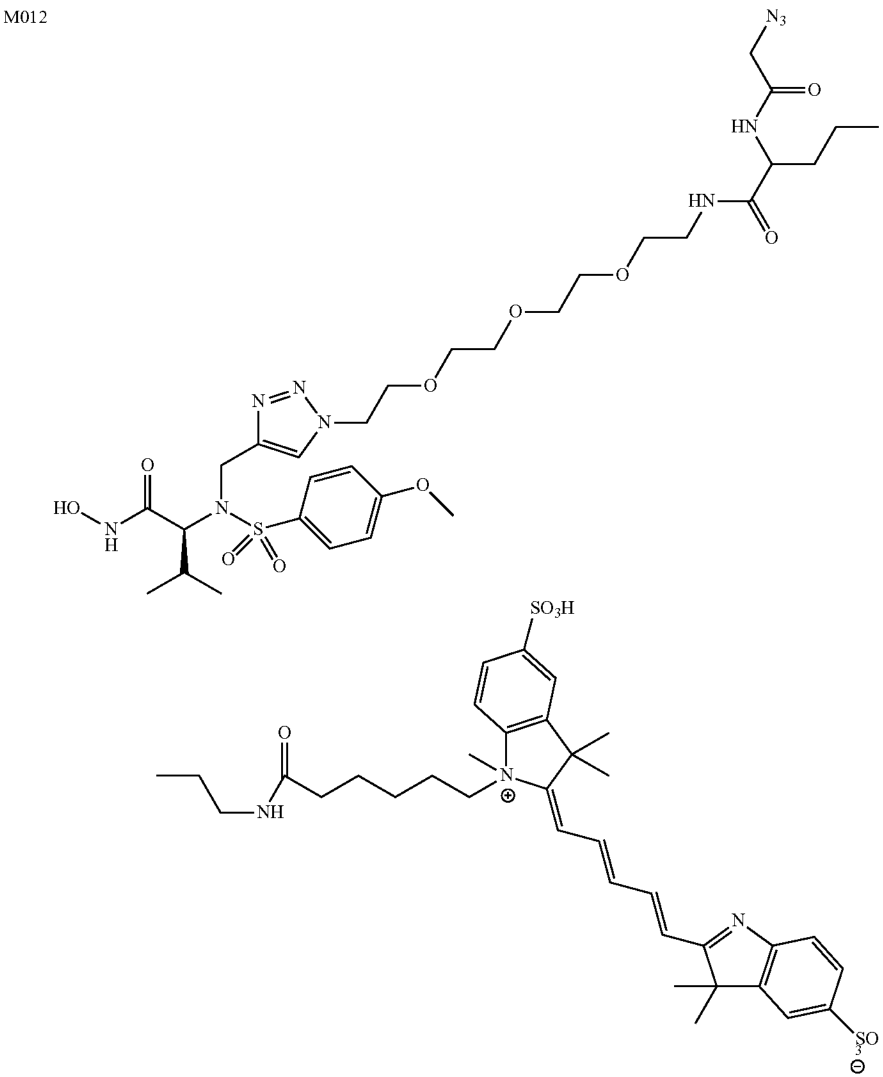 | | | 1% (10 nM) | 0% (10 nM) | 0% (10 nM) | 0% (10 nM) |
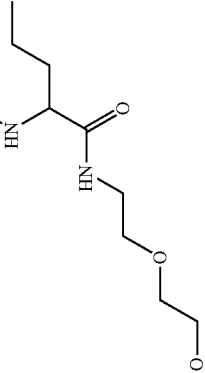

-continued
| ID | Structure | MW | cLogP | MMP-2 IC50, nM | MMP-8 IC50, nM | MMP-9 IC50, nM | MMP-13 IC50, nM |
|---|---|---|---|---|---|---|---|
| M013 | 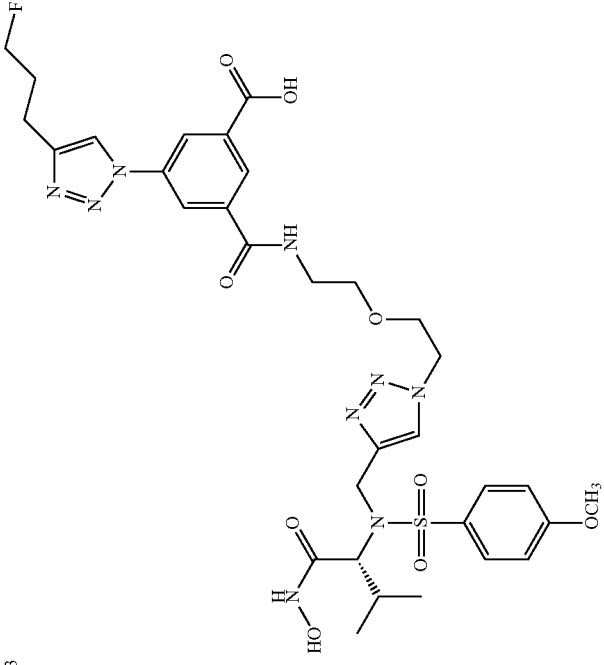 | | 2 | 66% (10 nM) | 84% (10 nM) | 67% (10 nM) | 79% (10 nM) |
| M014 | 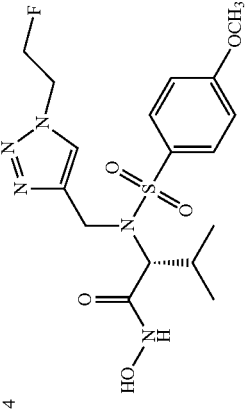 | 455.6 | 2.3 | | | | |

-continued

| ID | Structure | MW | cLogP | MMP-2 IC50, nM | MMP-8 IC50, nM | MMP-9 IC50, nM | MMP-13 IC50, nM |
|---|---|---|---|---|---|---|---|
| M015 | 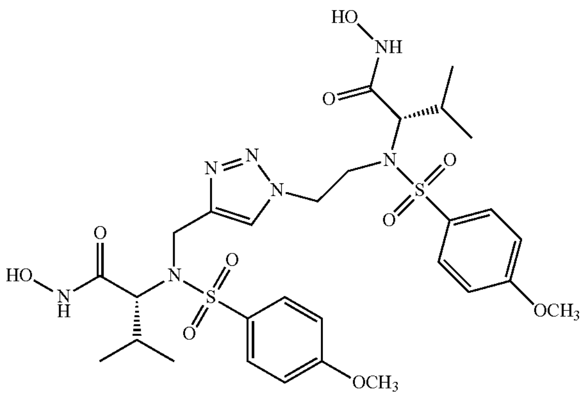 [SMILES: COc1ccc(S(=O)(=O)N(CCn2cc(CN([C@@H](C(=O)NO)C(C)C)S(=O)(=O)c3ccc(OC)cc3)nn2)[C@H](C(=O)NO)C(C)C)cc1] | 711.8 | 2 | | | | |
| M016 | 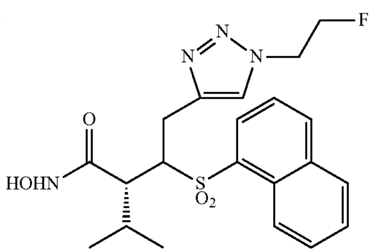 | 449.5 | 1.67 | | | | |

| ID | Structure | MW | cLogP | MMP-2 IC50, nM | MMP-8 IC50, nM | MMP-9 IC50, nM | MMP-13 IC50, nM |
|---|---|---|---|---|---|---|---|
| M017 | 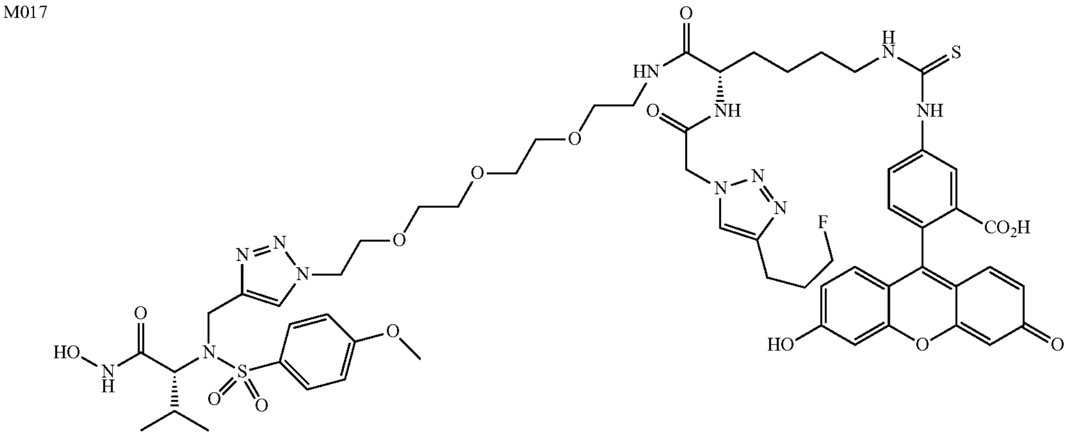 | 1245 | | | | | |
| M018 | 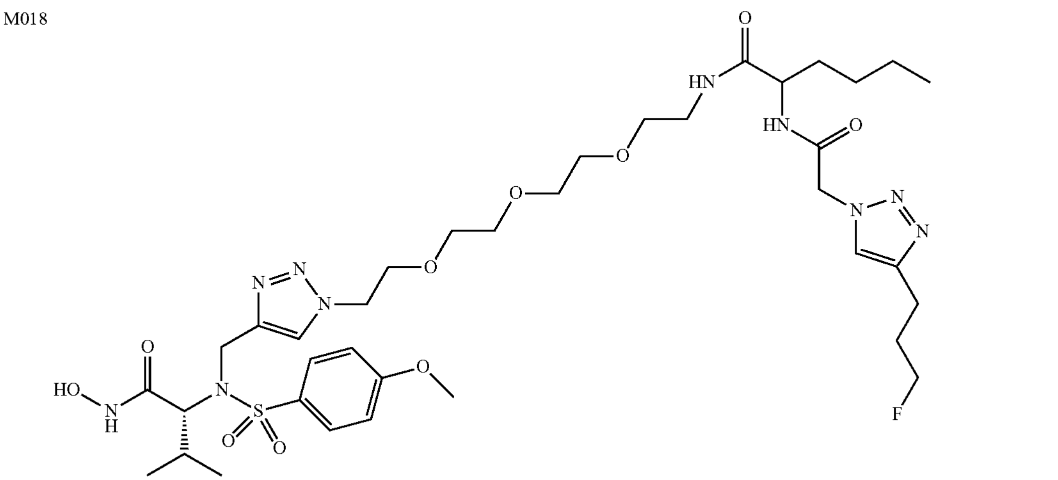 | 1481 | | | | | |

-continued

| ID | Structure | MW | cLogP | MMP-2 IC50, nM | MMP-8 IC50, nM | MMP-9 IC50, nM | MMP-13 IC50, nM |
|---|---|---|---|---|---|---|---|
| M019 | 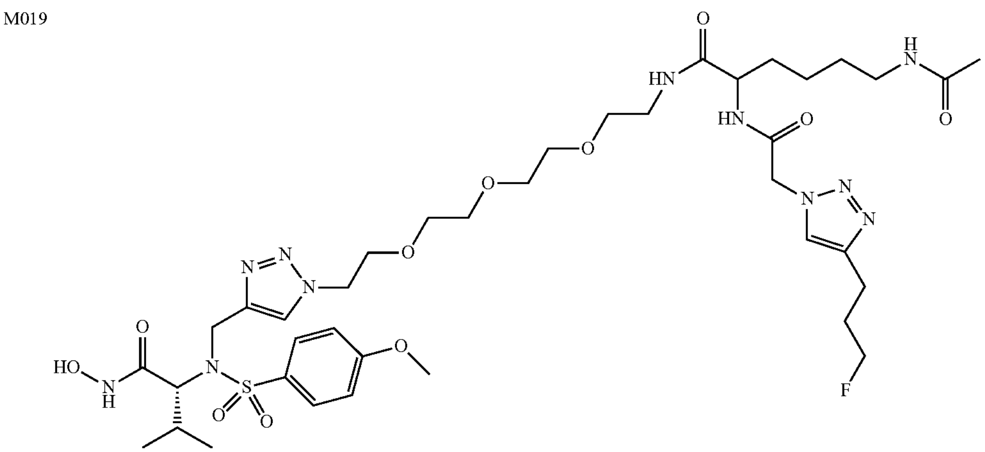 | 1644 | | | | | |

-continued
| ID | Structure | MW | cLogP | MMP-2 IC50, nM | MMP-8 IC50, nM | MMP-9 IC50, nM | MMP-13 IC50, nM |
|---|---|---|---|---|---|---|---|
| M020 | 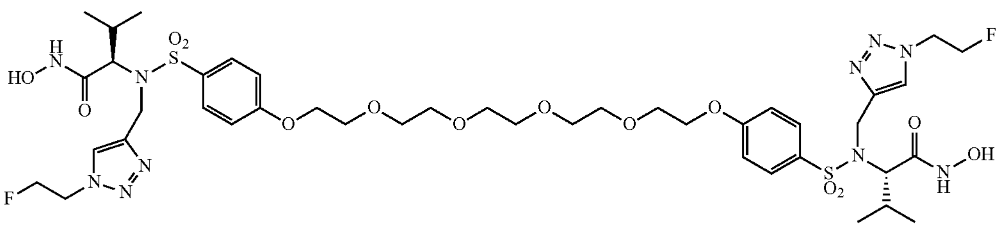 [SMILES: CC(C)[C@@H](C(=O)NO)N(Cc1cn(CCF)nn1)S(=O)(=O)c1ccc(OCCOCCOCCOCCOCCOc2ccc(S(=O)(=O)N(Cc3cn(CCF)nn3)[C@@H](C(=O)NO)C(C)C)cc2)cc1] | | | 1033 | | | |
| M021 | 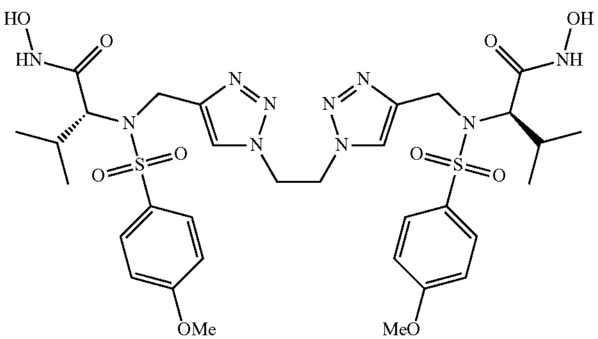 [SMILES: COc1ccc(S(=O)(=O)N(Cc2cn(CCn3cc(CN([C@@H](C(=O)NO)C(C)C)S(=O)(=O)c4ccc(OC)cc4)nn3)nn2)[C@@H](C(=O)NO)C(C)C)cc1] | 792.9 | 0.77 | | | | |
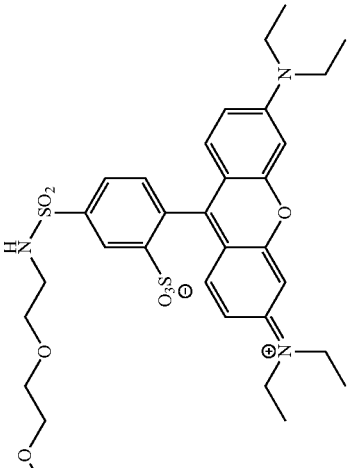

| ID | Structure | MW | cLogP | MMP-2 IC50, nM | MMP-8 IC50, nM | MMP-9 IC50, nM | MMP-13 IC50, nM |
|---|---|---|---|---|---|---|---|
| M022 | 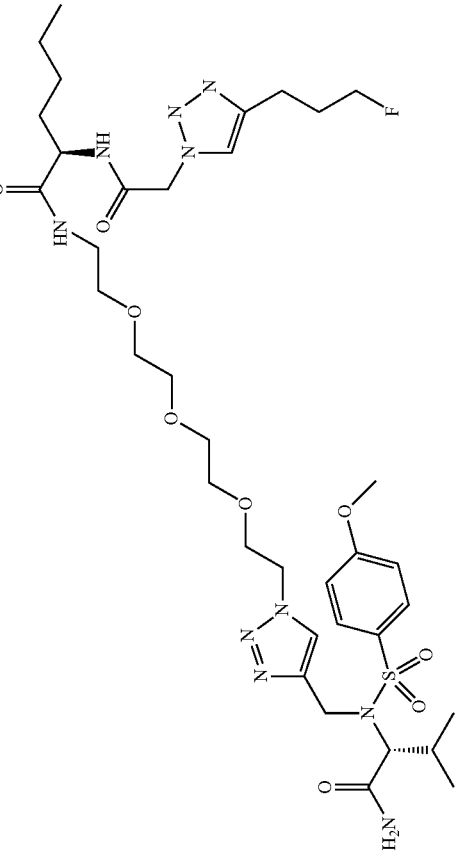 | 1739 | 0.77 | | | | |

| ID | Structure | MW | cLogP | MMP-2 IC50, nM | MMP-8 IC50, nM | MMP-9 IC50, nM | MMP-13 IC50, nM |
|---|---|---|---|---|---|---|---|
| M023 | 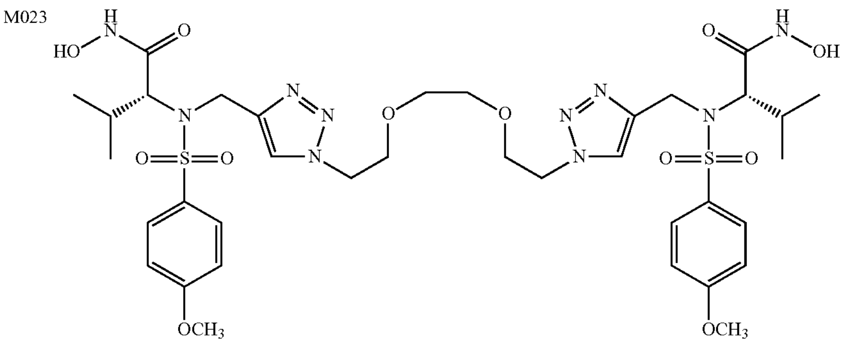 | 881 | | | | | |
| M024 | 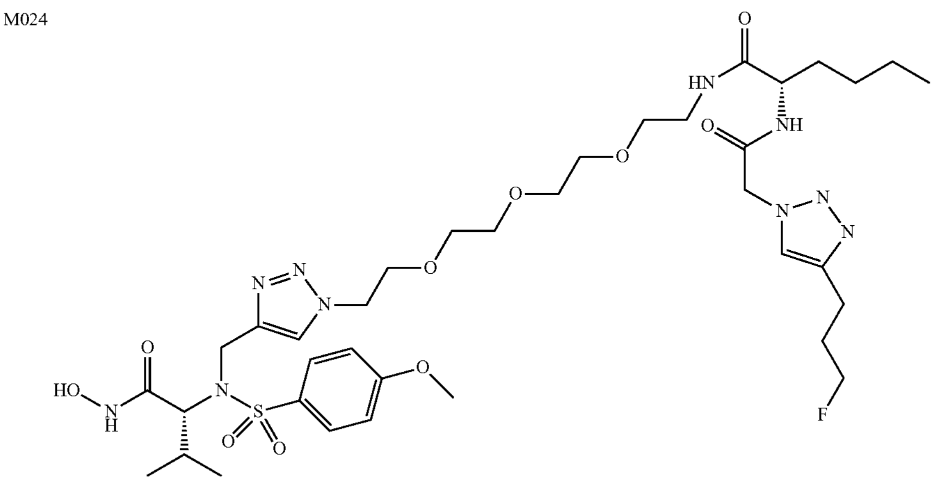 | 1422 | | | | | |

-continued
| ID | Structure | MW | cLogP | MMP-2 IC50, nM | MMP-8 IC50, nM | MMP-9 IC50, nM | MMP-13 IC50, nM |
|---|---|---|---|---|---|---|---|
| | 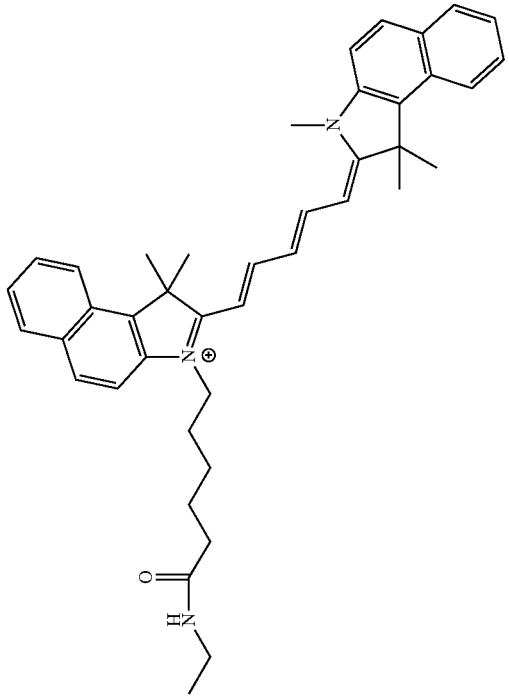 | | | | | | |

Any of the foregoing compounds may include a fluorophore or radiolabel. For example, M005 may be:

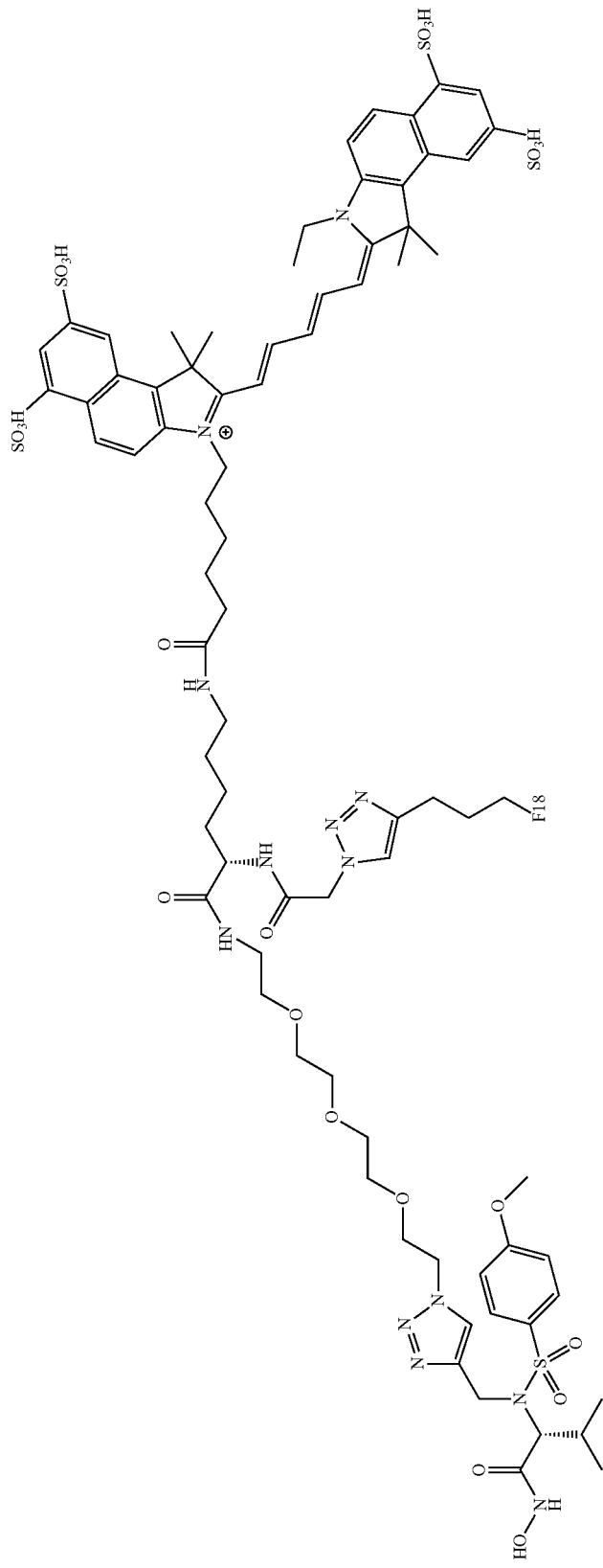

Embodiments of the present invention are shown below:
Proposed structures
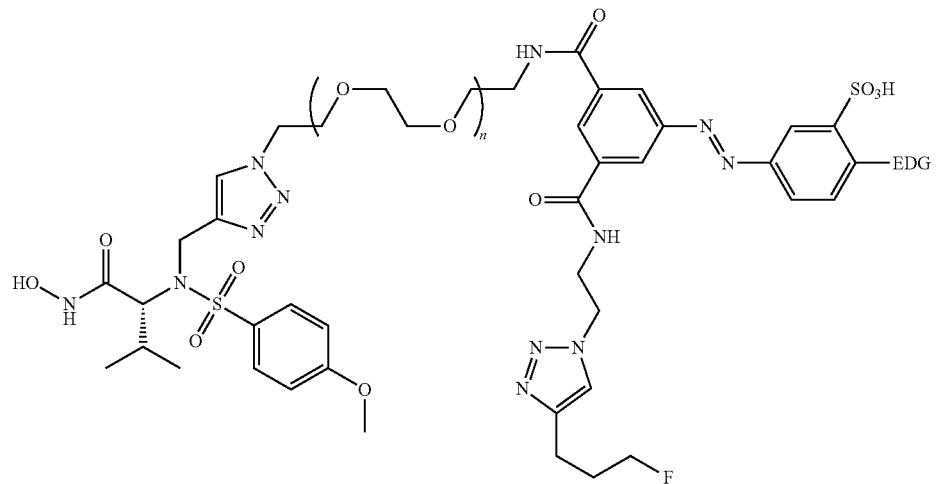
A
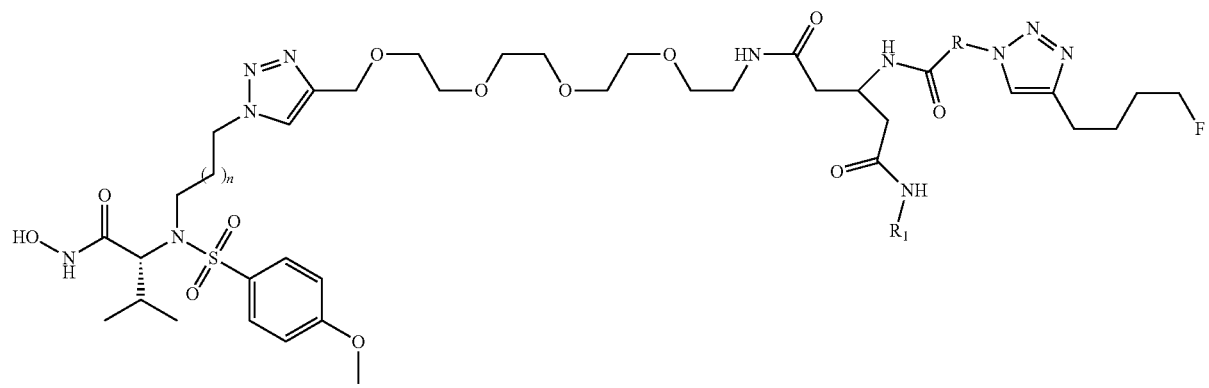
B
R1 = dye
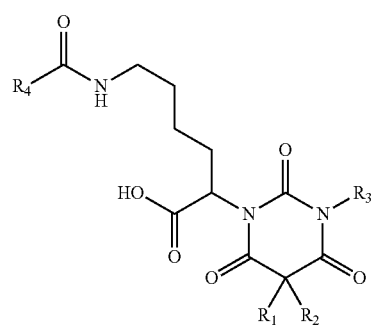
C
$R_1$, $R_2$ = Alkyl, cycloalkyl or Aryl group
$R_3$ = Alkyl, Aryl and aminoacid
$R_4$ = Alkyl, Aryl, heterocycle, etc

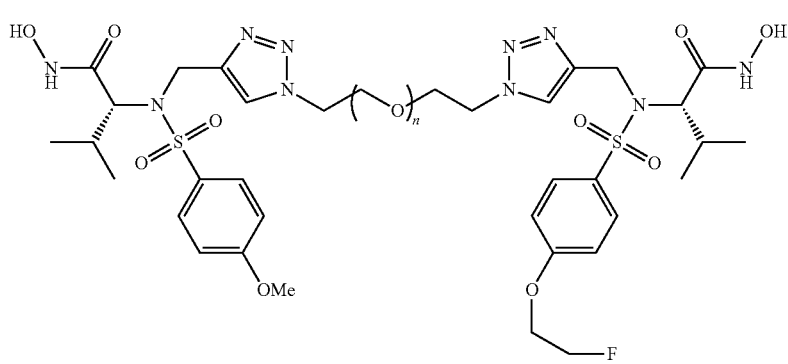
D
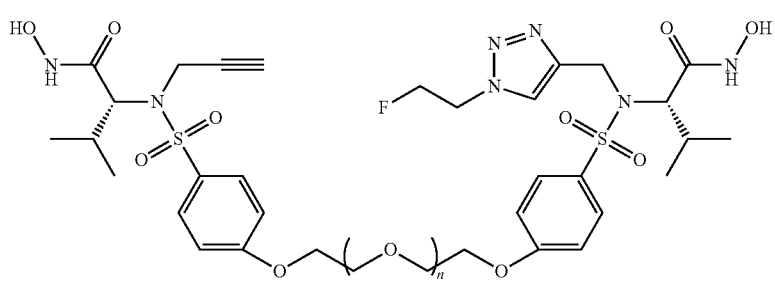
E
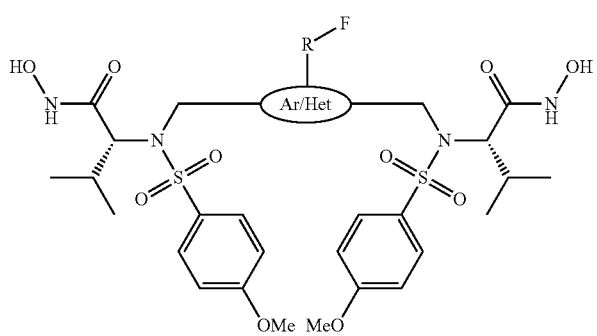
F
As one example, the M007 compound shows good MMP inhibition:
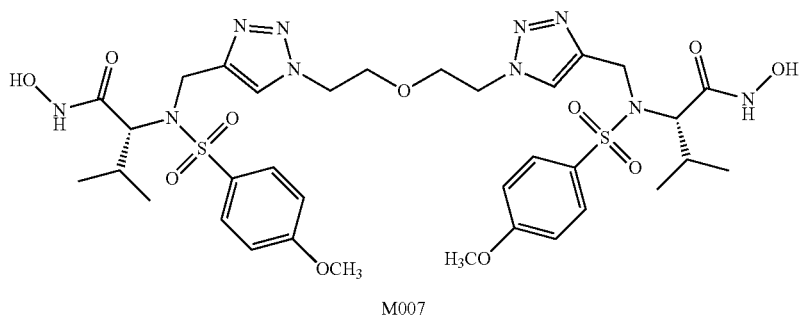
M007
MMP activity (% inhibition at 10 nM)
MMP-2  64%
MMP-8  94%
MMP-9  89%
MMP-13 96%

One example of the preparation of M007 analogs is shown below:
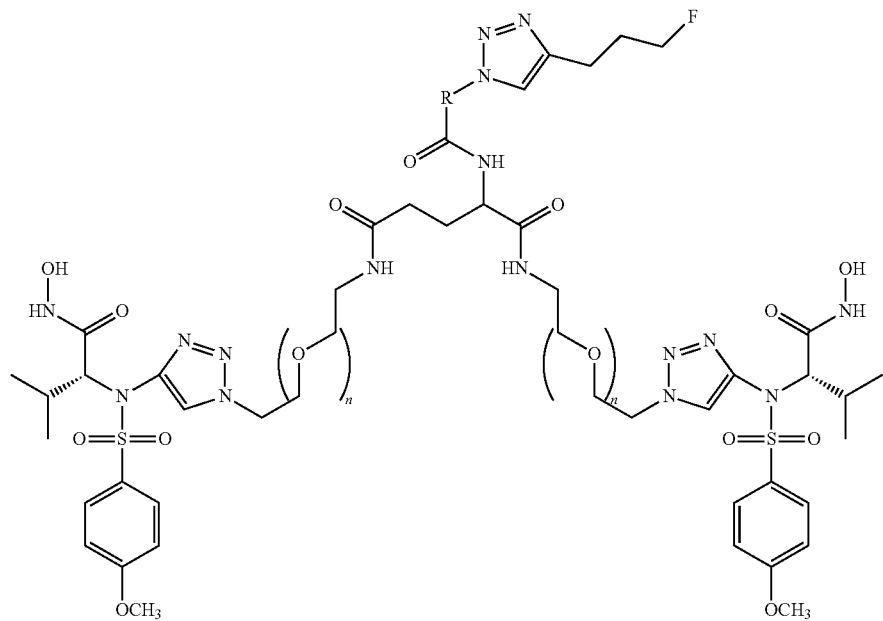
One example of a compound of the present invention is the Cy 5.5-[F18]-MMP tracer M005:
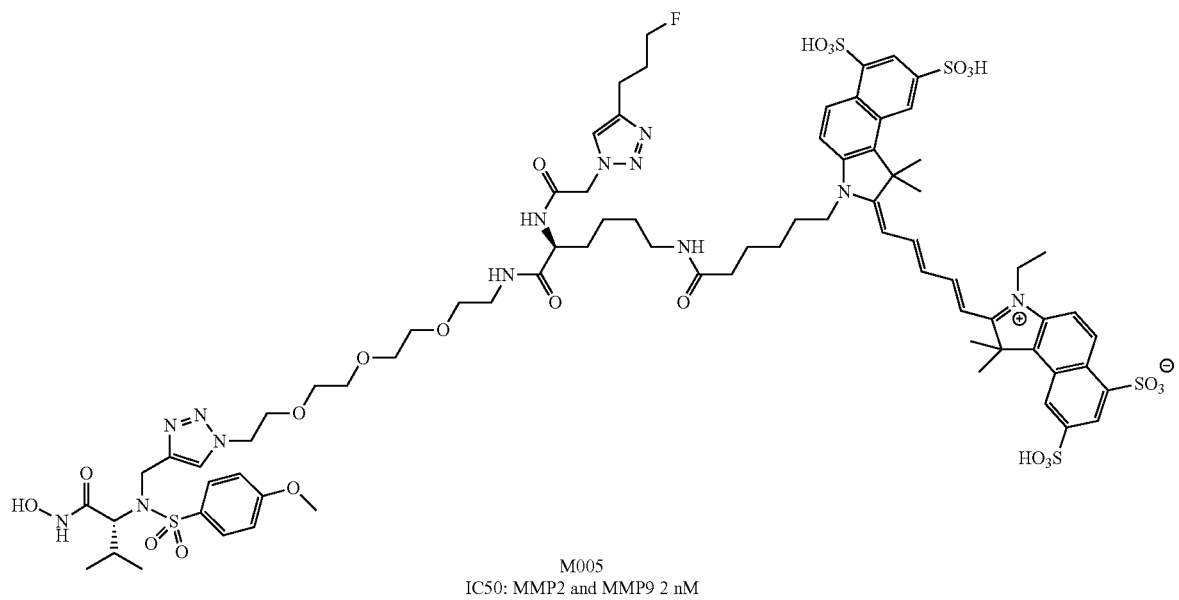
M005
IC50: MMP2 and MMP9 2 nM

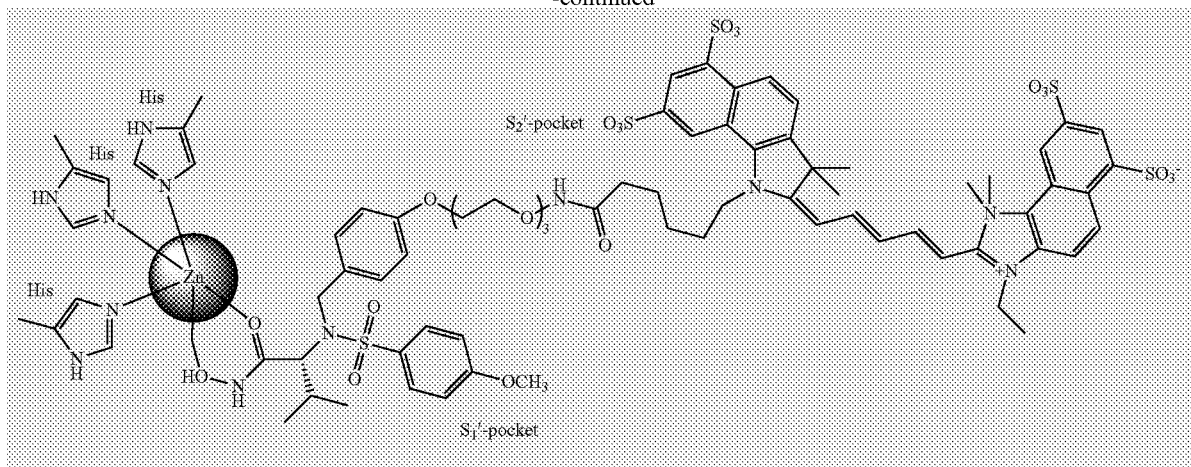

Figure 6:
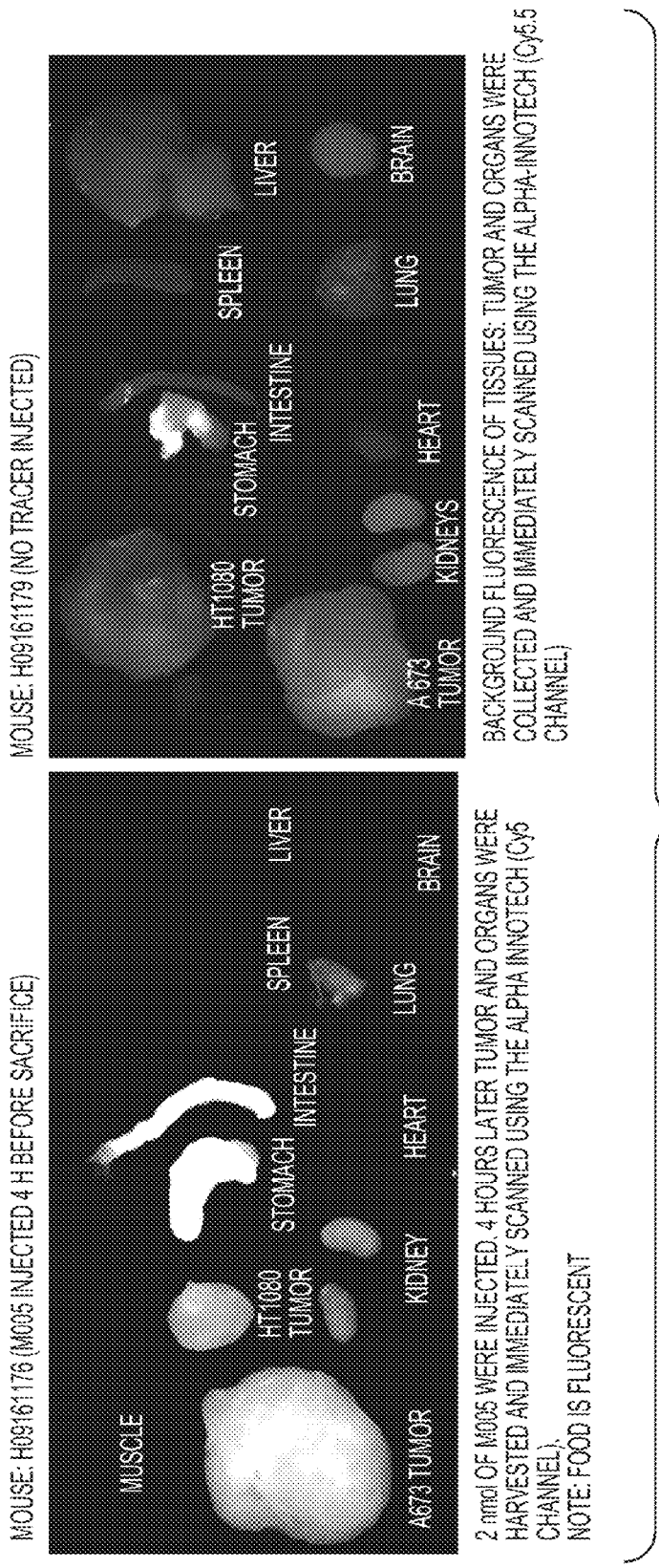
FIG. 6 shows biodistribution of M005: tumor and tissue scans (4 h uptake time, Cy5 channel, with and without tracer injection).
Figure 7:
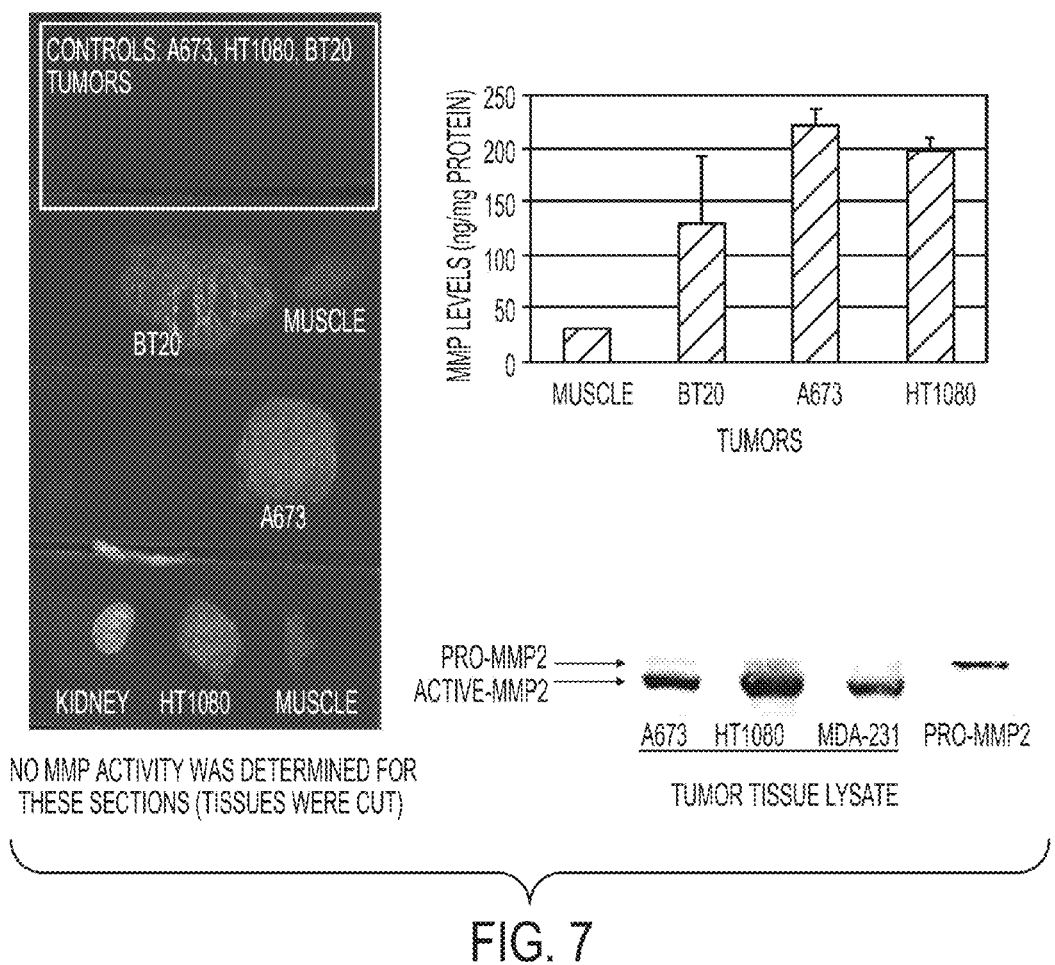
FIG. 7 shows tissue sections (10 µm) scan after M005 injection (uptake time: 4 h (Cy5.5 channel, Alpha-Innotech).
Figure 8:
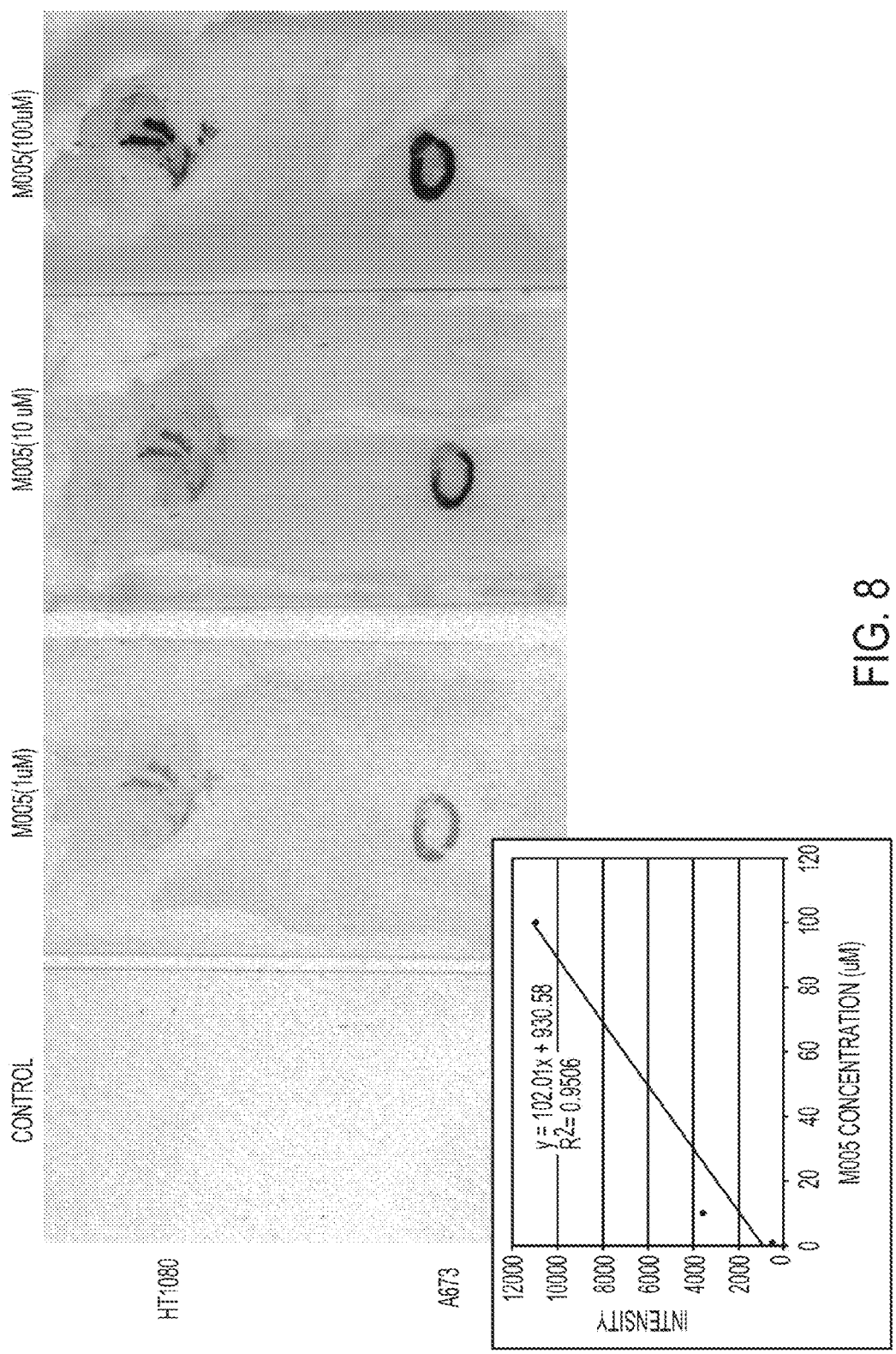
FIG. 8 shows M005 staining at different concentrations on tumor sections.
Figure 9:
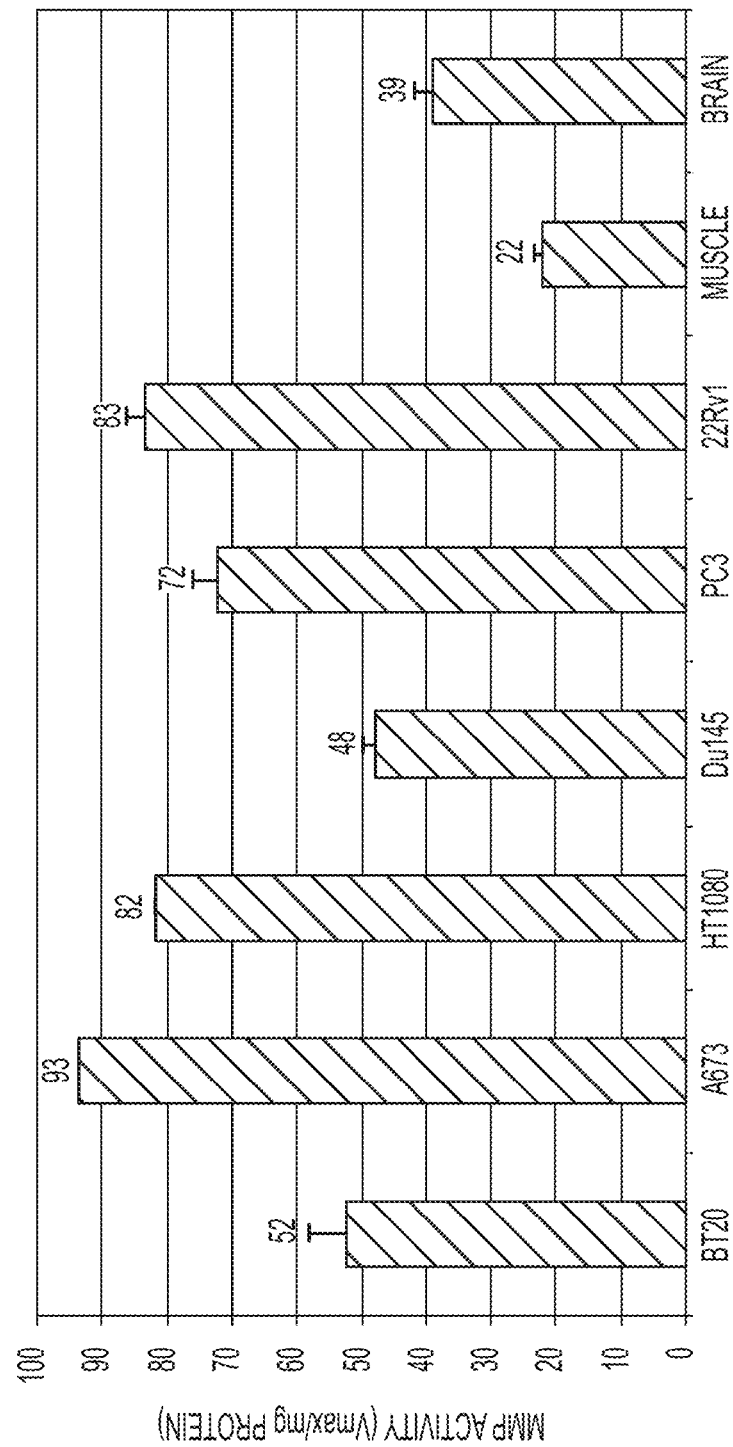
FIG. 9 shows average MMP activity measurement in mouse tissues.

FIG. 6 shows biodistribution of M005: tumor and tissue scans (4 h uptake time, Cy5 channel, with and without tracer injection). M005 shows uptake above background fluorescence of tissue. The brain was used as background tissue since there is no uptake of the tracer into the brain.

MMP Activity Measurement:

The activities were determined using Fluorimetric SensoLyte® 390 Generic MMP Activity Kit from Anaspec (cat #72202). This assay kit can detect the activity of several MMPs such as MMP-1, 2, 7, 8, 9, 13, 14, 15, 16 and 24.

For screening MMP compounds, activated 2 nM of recombinant MMP-2, 8, 9 or 13 are pre-incubated with MMP compound (inhibitor) for 30 min at 37° C. The substrate is added and the inhibition of MMP activity is expressed as % of total activity (without the inhibitor incubation).

For measuring the MMPs activity in biological samples, the substrate is mixed with sample lysate and immediately start measuring fluorescence intensity at Ex/Em=330 nm/390 nm continuously. The result is normalized by protein concentration.

The following describes an example of how at least one of the compounds of the present invention may be prepared. Other methods may be used and the below methods may be used to synthesize other compounds described herein.

Synthesis of M005 precursor

To a vial charged with compound 1 (S)-6-amino-2-(2-azidoacetamido) N (2 (2 (2 (2-(4-((N—((R)-1-(hydroxyamino)-3-methyl-1-oxobutan-2-yl)-4-methoxyphenylsulfonamido) methyl)-1H-1,2,3-triazol-1-yl)ethoxy)ethoxy)ethoxy)ethyl) hexanamide (5.32 mg, 6.14 umol) and Cy5.5-NHS ester (6.60 mg, 5.85 umol) in DMF (0.2 ml), was added triethylamine DMF solution (0.1 M, 120 ul, 12 umol) via a micro syringe drop wise. The mixture was stirred at room temperature in dark for 30 min until LCMS indicated complete consumption of the Cy5.5-NHS ester. The reaction was solution was diluted with HCl (aq 0.1 M, 0.4 mL), injected to a semi preparative reversed-phase HPLC with Phenomenex Gemini C-18 (250×21.20 mm). The fraction containing M005 precursor was eluted with mobile phase (0.15% TFA in acetonitrile and water, 30 min gradient method 10% to 90% acetonitrile in water) and afforded M005 precursor (4.80 mg, 2.88 umol, yield 49.2%) after lyophilization. $^1$H NMR (400 MHz, D$_2$O): δ 8.34-8.32 (d, J=9.2 Hz, 2H), 8.23 (s, 2H), 7.89 (s, 2H), 7.68-7.52 (m, 2H), 7.24-7.10 (m, 3H), 6.89 (d, J=8.8 Hz, 2H), 6.26 (d, J=8.8 Hz, 2H), 5.98 (m, 1H), 5.70-5.48 (m, 2H), 4.01 (d, J=12.0 Hz, 1H), 3.90 (m, 2H), 3.65-3.55 (m, 2H), 3.46 (s, 4H), 3.22-3.16 (m, 5H), 3.07 (d, J=10.8 Hz, 1H), 2.93-2.91 (m, 10H), 2.82-2.70 (m, 2H), 2.40-2.35 (m, 2H), 1.65-1.52 (m, 3H), 1.42-1.35 (m, 12H), 1.20 (m, 2H), 1.00 (m, 4H), 0.88-0.55 (m, 10H), 0.23 (d, J=6.0 Hz, 3H), 0.08 (d, J=6.4 Hz, 3H). Mass Spec (lo-res): Calc'd for C$_{72}$H$_{93}$N$_{13}$O$_{23}$S$_5$: 1667.5. Found: 835.0 (M+2H$^+$)/2.

Synthesis of M005 Reference Standard

Compound 1 (5.00 mg, 6 umol) was added to a vial contains CuSO$_4$ (aq 0.1 M, 0.1 ml, 10 umol), sodium ascorbate (0.50 mg, 1.7 umol) in DMF (0.2 mL). 5-fluoropent-1-yne (8.60 mg, 0.1 mmol) in THF (20 uL) was added. The mixture was stirred at room temperature for 30 min until LCMS indicated the full conversion of the reaction. The mixture was purified on HPLC with the same condition described above. The fraction contains click reaction product (4.0 mg) was dried on lyophilizer overnight and used directly. To a vial contains the click product (1.69 mg, 1.97 umol), was added Cy5.5-NHS ester (2.00 mg, 1.97 umol) in DMF (0.2 ml) and triethylamine (0.1M in DMF, 20 ul). The reaction was stirred in dark for 48 hours, diluted with HCl (aq 0.1 M, 0.3 ml), and purified on HPLC using the same condition described above. The fraction contains M005 reference standard was dried by overnight lyophilization to afford M005 reference standard (2.60 mg, 1.48 umol, yield 75%) $^1$H NMR (400 MHz, D$_2$O)

δ 8.34-8.32 (d, J=9.2 Hz, 2H), 8.23 (s, 2H), 7.89 (s, 2H), 7.68-7.52 (m, 2H), 7.24-7.10 (m, 4H), 6.89 (d, J=8.8 Hz, 2H), 6.26 (d, J=8.8 Hz, 2H), 5.98 (m, 1H), 5.70-5.48 (m, 2H), 4.70 (s, 2H), 4.01-3.90 (m, 5H), 3.65-3.46 (m, 4H), 3.22-3.16 (m, 5H), 3.07 (d, J=10.8 Hz, 1H), 2.93-2.91 (m, 10H), 2.82-2.70 (m, 2H), 2.40-2.35 (m, 2H), 2.20-2.18 (m, 2H), 1.65-1.52 (m, 3H), 1.42-1.35 (m, 12H), 1.20 (m, 2H), 1.00 (m, 4H), 0.88-0.55 (m, 10H), 0.23 (d, J=6.0 Hz, 3H), 0.08 (d, J=6.4 Hz, 3H). $^{19}$F NMR (376 MHz, D$_2$O): −219.07 (tt, J=47 Hz, 27 Hz). Mass Spec (lo-res): Calc'd for $C_{77}H_{100}FN_{13}O_{23}S_5$: 1753.6. Found: 877.9 (M+2H$^+$)/2.

Radiosynthesis of [18F]M005

A vial containing the click chemistry mixture of M005-precursor (2 mg), dissolved in 250 µL of 0.1 M CuSO$_4$, sodium ascorbate (20 mg), ACN (0.25 mL) and EtOH/H$_2$O (2:1 ratio, 0.25 mL total). Aqueous $^{18}$F-fluoride ion, produced in the cyclotron target, was passed through an anion exchange resin cartridge. The $^{18}$O—H$_2$O was retained for recycling. The $^{18}$F fluoride was eluted from the column using a solution of potassium carbonate (3 mg) in water (0.4 mL) and collected into the reaction vessel. Kryptofix® 222 (20 mg) dissolved in acetonitrile (1 mL) was added to the aqueous $^{18}$F-fluoride in the reaction vessel. The mixture was dried by heating between 68-95° C. under reduced pressure (250 mbar) and a stream of argon. After the $^{18}$F-fluoride was considered sufficiently activated (as indicated by a constant pressure reading for the reactor while under vacuum), the tosylate precursor was then added as a solution in anhydrous MeCN (20 mg in 0.8 mL). The reaction was heated closed at 135° C. for 3-5 mM for fluorination. After fluorination, the transfer line in the reaction vessel was kept above the surface of the reaction mixture and opened for approximately 20 seconds to allow the transfer of $^{18}$F-pentyne from the reaction pot into the click vial (via bubbling of the labeled pentyne into the click solution) with the HPLC transfer line held above the reaction mixture. After the transfer was complete, the click reaction was allowed to proceed for 20 min. After clicking, the transfer line was lowered into the click solution and the contents were pressurized through the HPLC load vial for dilution with water prior to purification. The reaction mixture containing crude $^{18}$F-M005 was transferred to the HPLC sample loop (5 mL) and purified via chromatographic separation using a semi-preparative HPLC column (Phenomenex Gemini, C18, 5µ, 10×250 mm) using a isocredit 30% MeCN in 20 mM Phosphate buffer (pH=7.6) at 5 mL/min. The column effluent was monitored using UV (210, 254 or 280 nm) and radiometric detectors connected in series. Purified $^{18}$F-M005 was collected from the column at the retention time window determined for the M005 reference standard, which coincides with the time that the radiometric detectors begin showing the main peak. The retention time of the $^{18}$F-M005 in this system was approximately 33 minutes. The purified $^{18}$F-M005 fraction, eluted from the HPLC purification column, was diluted with water (40 mL) and captured onto a C18 SepPak cartridge. The C18 SepPak cartridge was washed with water (10 mL) followed by elution of the product with 0.5 mL of EtOH. The sample was then diluted with sterile water (4.5 mL of water) to afford a final formulation of $^{18}$F-M005 in a maximum of 10% EtOH:water. For sterile preparations, the dose was filtered through a sterile Pall 0.2 um filter.

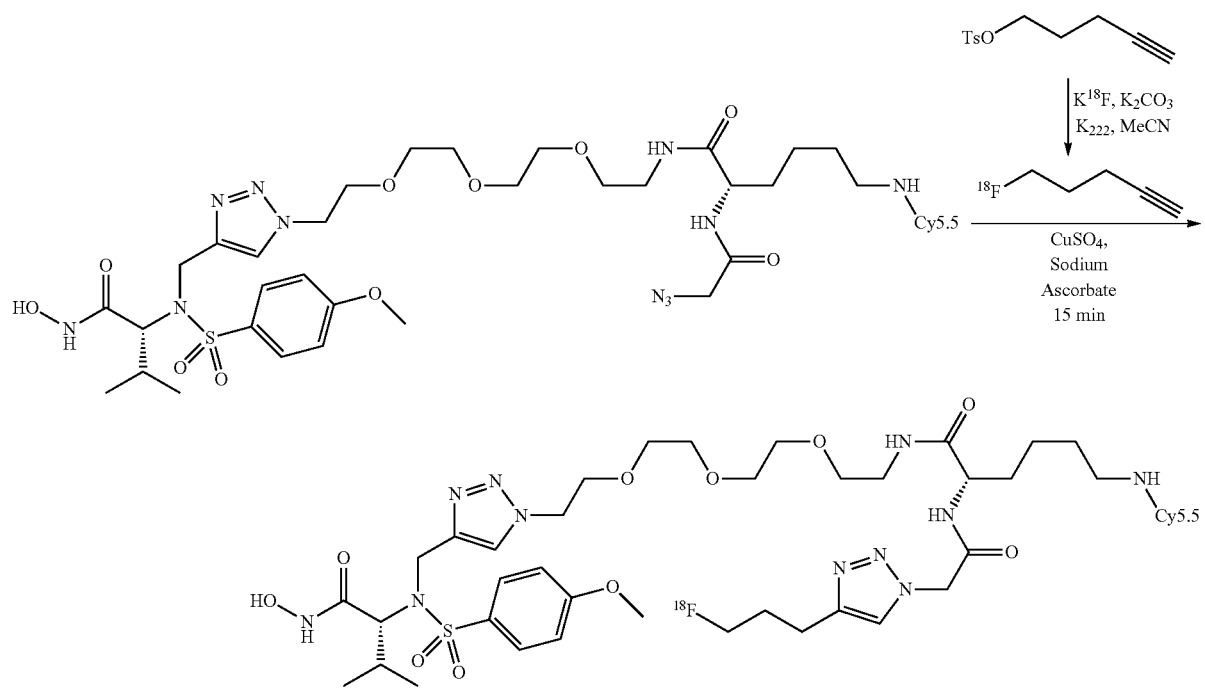

Radiosynthesis of [18F]M005
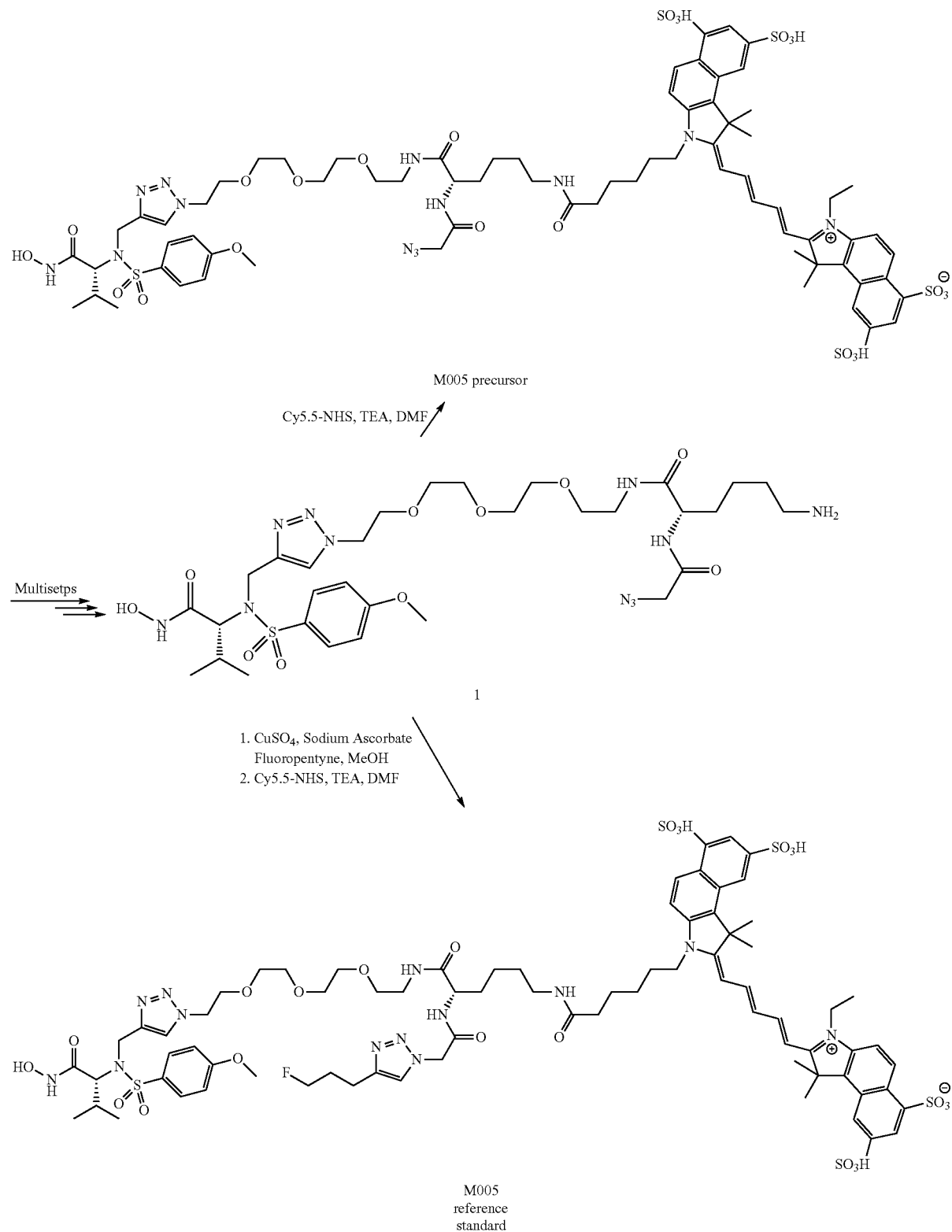

Chemical syntheses of M005 precursor and reference standard.

In one embodiment, the invention is a compound of the Formula (I):

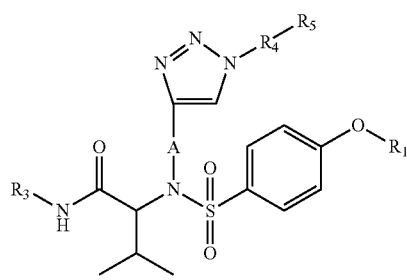

and pharmaceutically acceptable salts and stereoisomers thereof, wherein:

$R_1$ is selected from the group consisting of: $C_{1-6}$alkyl, $C_{1-6}$alkyl-halo, protecting group or leaving group;

A is a bond, $(-CH_2-)_{1-5}$, or is $(-CH_2-CH_2-O-)_{1-5}$;

$R_3$ is selected from the group consisting of: OH, $NH_2$, protecting group or leaving group;

$R_4$ is a bond or is at least one selected from the group consisting of: aryl, heteroaryl, $C_{1-20}$alkyl, wherein at least one C of $C_{1-20}$alkyl is optionally replaced by O, S, NH, C(O), aryl or heteroaryl and wherein at least one H of $C_{1-20}$alkyl is optionally replaced with OH, $NH_2$, COOH, $C_{1-8}$alkyl, $C_{1-8}$alkyl-halo, wherein at least one C of $C_{1-8}$alkyl is optionally replaced by O, S, C(O), aryl, heteroaryl or NH, $R_5$ is selected from the group consisting of: H, halo, $CH_3$, $NH_2$, OH, $SO_2$, $NO_2$, $-O-C_{1-6}$alkyl,

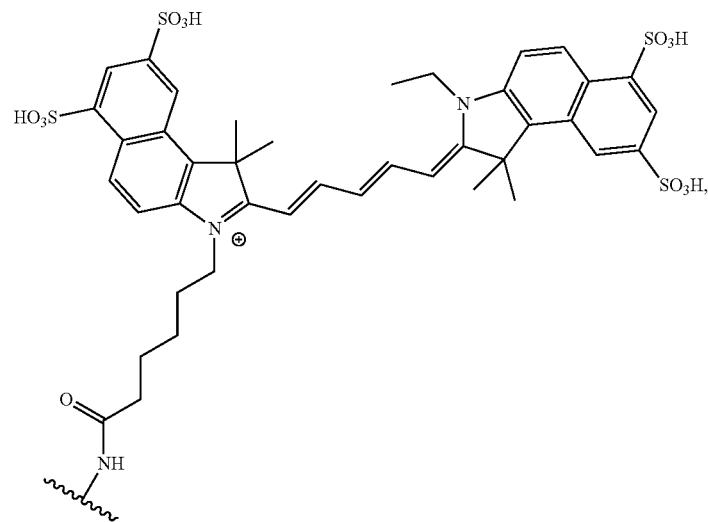

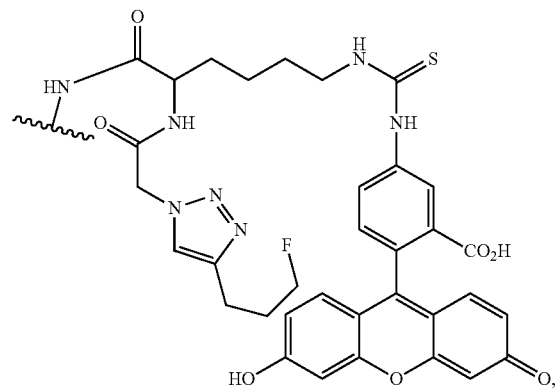

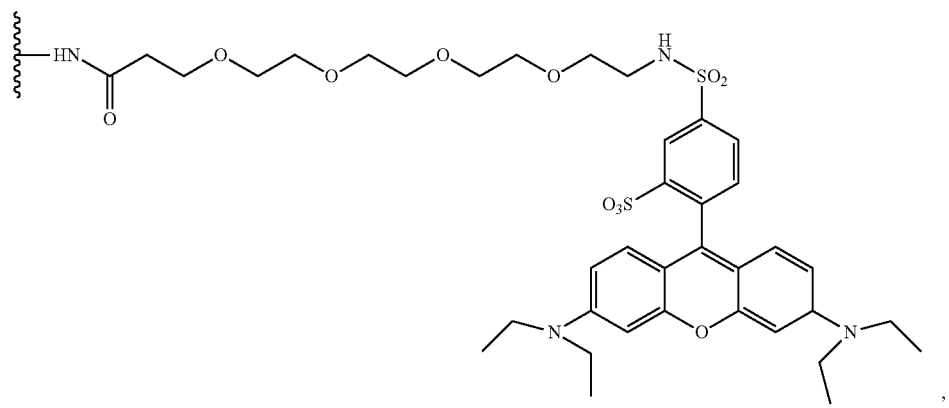

$C_{1-20}$alkyl, $C_{1-20}$alkyl-aryl, $C_{1-20}$alkyl-heteroaryl,
  wherein at least one C of the $C_{1-20}$alkyl is optionally replaced with S, $SO_2$, C(O), C(S), aryl, heteroaryl or NH,
  wherein at least one H of the $C_{1-20}$alkyl, aryl or heteroaryl is replaced with halo, OH, COOH, $SO_3$, $NH_3$, $N(alkyl)_2$, $C_{1-8}$alkyl, $C_{1-8}$alkyl-halo,
    wherein at least one C of $C_{1-8}$alkyl is optionally replaced by O, S, C(O), aryl, heteroaryl or NH,
  wherein at least one H or halo is optionally replaced with a radionuclide or a fluorophore.

In another embodiment, the invention is a compound of Formula (I) wherein A is a bond.

In another embodiment, the invention is a compound of Formula (I), wherein $R_1$ is $C_{1-6}$alkyl.

In another embodiment, the invention is a compound of Formula (I), wherein $R_3$ is OH.

In another embodiment, the invention is a compound of Formula (I), wherein $R_5$ is a halo or a radionuclide.

In another embodiment, the invention is a compound of Formula (I), wherein $R_4$ is $C_{1-20}$alkyl, wherein at least one C of $C_{1-20}$alkyl is optionally replaced by O, S, NH, C(O).

In another embodiment, the invention is a compound of Formula (I), that is:

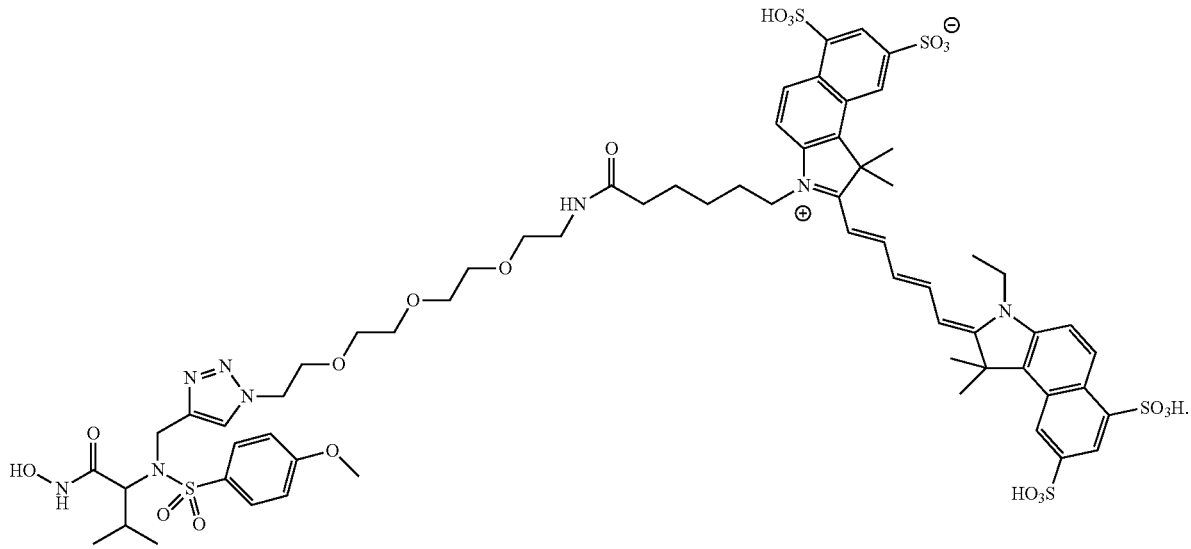

In another embodiment, the invention is a compound of Formula (I), that is:

In another embodiment, the invention is a compound of Formula (I), wherein R₄ is aryl.

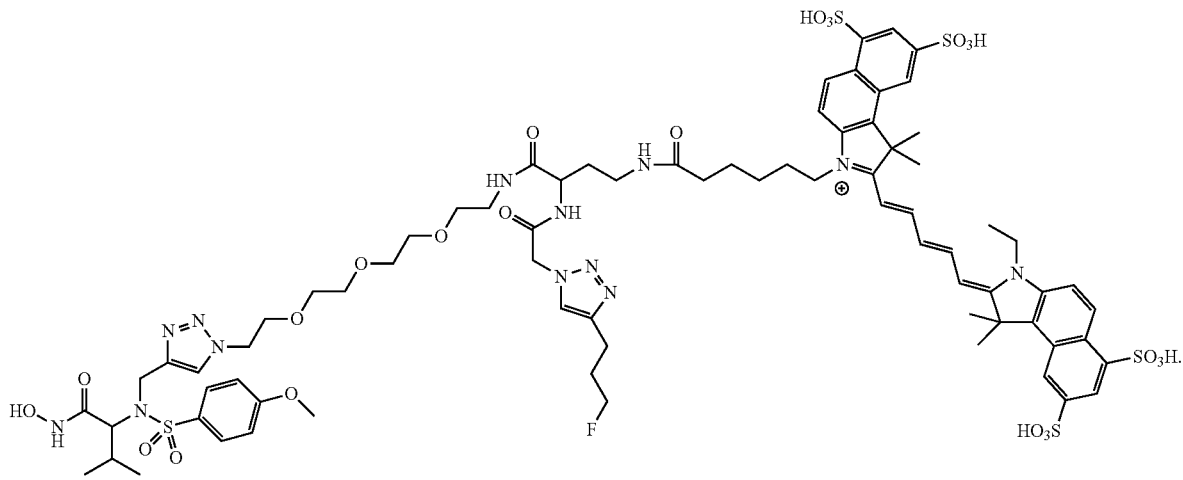 [SMILES: CCN1\C(=C/C=C/C=C/C2=[N+](CCCCCC(=O)NCCC(NC(=O)Cn3cc(CCCF)nn3)C(=O)NCCOCCOCCOCCn3cc(CN(C(C(=O)NO)C(C)C)S(=O)(=O)c4ccc(OC)cc4)nn3)c3ccc4c(S(=O)(=O)O)cc(S(=O)(=O)O)cc4c3C2(C)C)C(C)(C)c2c1ccc1c(S(=O)(=O)O)cc(S(=O)(=O)O)cc21]

In another embodiment, the invention is a compound of Formula (I), that is:

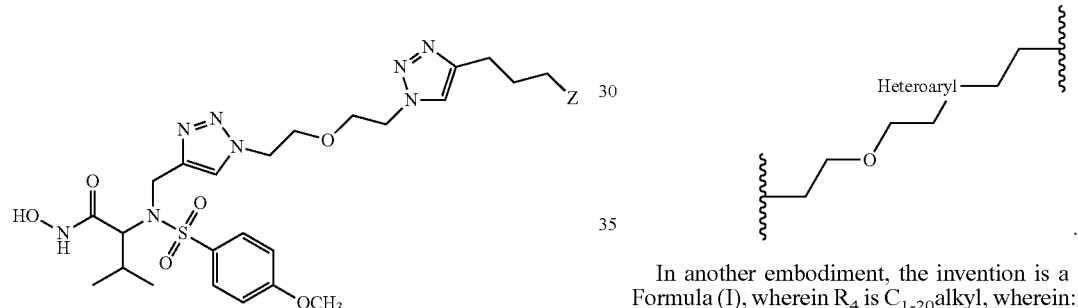

wherein Z is a halo or a radionuclide.

In another embodiment, the invention is a compound of Formula (I), that is:

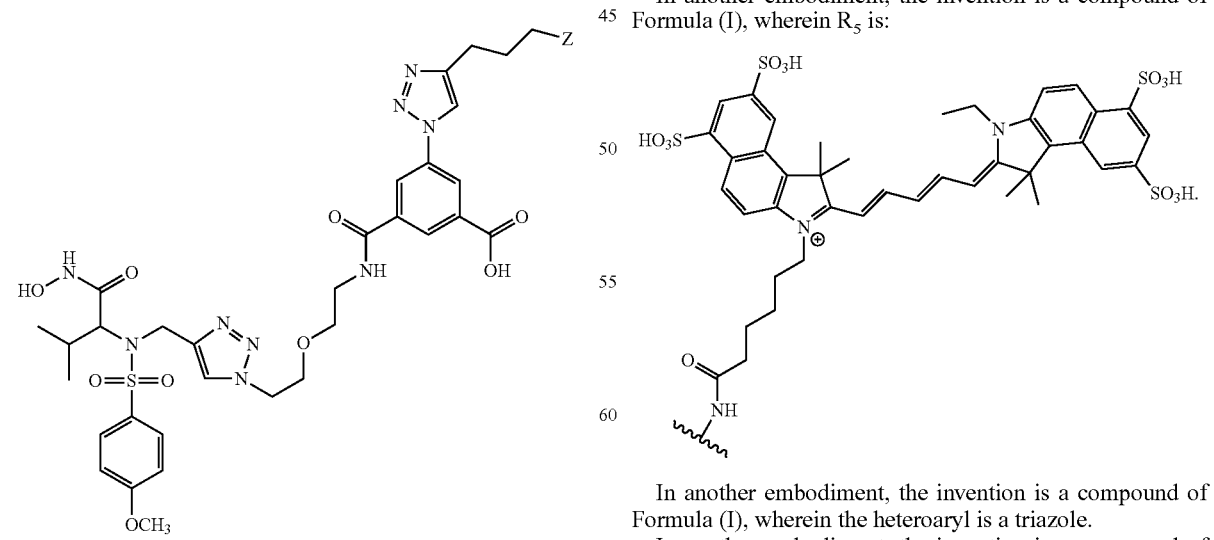

wherein Z is a halo or a radionuclide.

In another embodiment, the invention is a compound of Formula (I), wherein R₄ is:

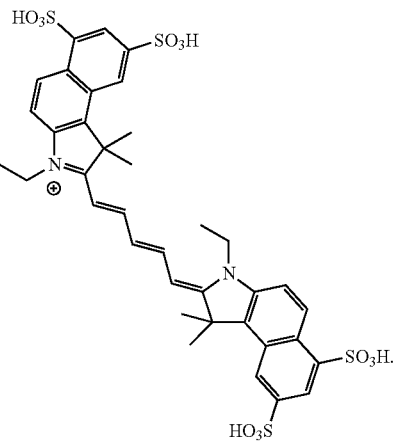

In another embodiment, the invention is a compound of Formula (I), wherein R₄ is $C_{1-20}$alkyl, wherein: at least one C of $C_{1-20}$alkyl is replaced by O, at least one C of $C_{1-20}$alkyl is replaced by C(O)NH, at least one C of $C_{1-20}$alkyl is replaced by aryl, at least one C of $C_{1-20}$alkyl is replaced by heteroaryl, wherein at least one H of the aryl is replaced by COOH.

In another embodiment, the invention is a compound of Formula (I), wherein R₄ is —[(CH₂)₂—O]₁₋₆—.

In another embodiment, the invention is a compound of Formula (I), wherein R₅ is:

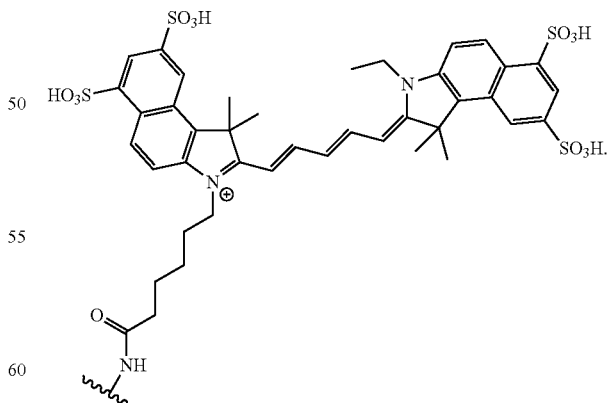

In another embodiment, the invention is a compound of Formula (I), wherein the heteroaryl is a triazole.

In another embodiment, the invention is a compound of Formula (I), wherein at least one H of $C_{1-20}$alkyl is replaced with

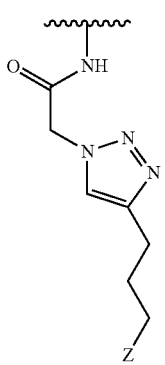

wherein Z is a halo or a radionuclide.

In another embodiment, the invention is a compound of Formula (I), wherein $R_4$ is

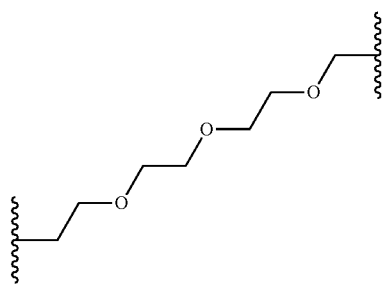

In another embodiment, the invention is a compound of Formula (II):

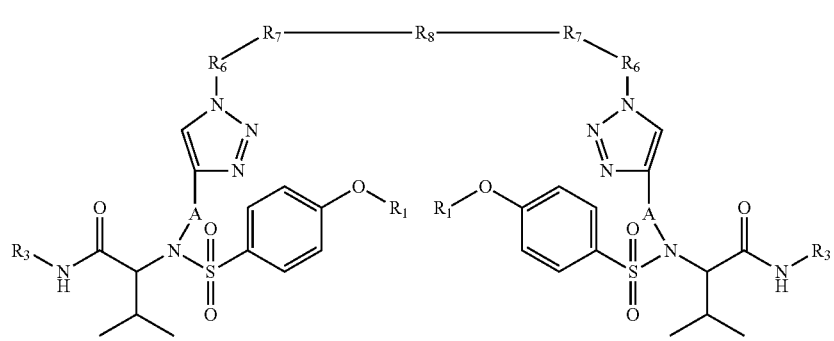

and pharmaceutically acceptable salts and stereoisomers thereof,
wherein:
each $R_1$ is independently selected from the group consisting of: $C_{1-6}$alkyl, $C_{1-6}$alkyl-halo, protecting group or leaving group;
each A is a bond, $(CH_2)_{1-5}$, or is $(-CH_2-CH_2-O-)_{1-5}$;
each $R_3$ is independently selected from the group consisting of: OH, $NH_2$, protecting group or leaving group;
each $R_6$ is independently a bond or is at least one selected from the group consisting of: aryl, heteroaryl, or $C_{1-20}$alkyl, wherein at least one C of $C_{1-20}$alkyl is optionally replaced by O, S, NH, C(O), aryl or heteroaryl and wherein at least one H of $C_{1-20}$alkyl is optionally replaced with OH, $NH_2$, $C_{1-8}$alkyl, $C_{1-8}$alkyl-halo, wherein at least one C of $C_{1-8}$alkyl is optionally replaced with at least one of O, S, C(O), NH, aryl and heteroaryl;
each $R_7$ is independently a bond or is at least one selected from the group consisting of: $CH_2$, NH, C(O)NH, $C_{1-6}$alkyl, wherein at least one C of $C_{1-6}$alkyl is optionally replaced by O, S, NH, C(O) and wherein at least one H of $C_{1-6}$alkyl is optionally replaced by OH, $NH_2$, $SO_2$, $C_{1-8}$alkyl, $C_{1-8}$alkyl-halo,
wherein at least one C of $C_{1-8}$alkyl is optionally replaced by O, S, C(O), aryl, heteroaryl or NH,
$R_8$ is a bond or is at least one selected from the group consisting of: O, NH, S, aryl, heteroaryl, wherein at least one H of aryl or heteroaryl is optionally replaced with $C_{1-8}$alkyl, $C_{1-8}$alkyl halo, wherein at least one C of $C_{1-8}$alkyl is optionally replaced with at least one of O, S, C(O), NH, aryl and heteroaryl;
$(CH_2)_{1-6}$, wherein at least one C of $(CH_2)_{1-6}$ is optionally replaced by O, NH or S;
wherein at least one H or halo is optionally replaced with a radionuclide or a fluorophore.

In another embodiment, the invention is a compound of Formula (II), wherein each A is a bond.

In another embodiment, the invention is a compound of Formula (II), wherein each $R_3$ is OH.

In another embodiment, the invention is a compound of Formula (II), wherein each $R_1$ is $CH_3$.

In another embodiment, the invention is a compound of Formula (II), wherein each $R_6$ is a bond.

In another embodiment, the invention is a compound of Formula (II), wherein $R_8$ is O.

In another embodiment, the invention is a compound of Formula (II), wherein each $R_7$ is $C_{1-6}$alkyl.

In another embodiment, the invention is a compound of Formula (II), wherein each $R_6$ is $C_{1-20}$alkyl, wherein at least one C of $C_{1-20}$alkyl is optionally replaced by O, S, NH, C(O), aryl or heteroaryl and wherein at least one H of $C_{1-20}$alkyl is optionally replaced with OH, $NH_2$, $C_{1-8}$alkyl-halo, wherein at least one C of $C_{1-8}$alkyl is optionally replaced with at least one of O, S, C(O), NH, aryl and heteroaryl.

In another embodiment, the invention is a compound of Formula (II), wherein each $R_6$ is $-[(CH_2)_2-O]_{1-6}-$.

In another embodiment, the invention is a compound of Formula (II), wherein each

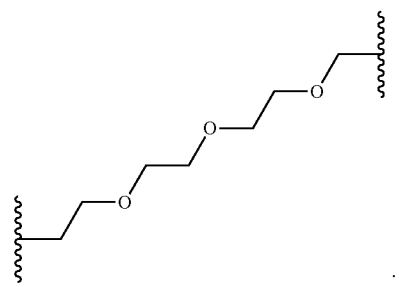 [SMILES: *CCOCCOCCOC*]

In another embodiment, the invention is a compound of Formula (II), wherein each $R_7$ is $C_{1-6}$alkyl, wherein at least one C of $C_{1-6}$alkyl is optionally replaced by O, S, NH, C(O) and at least one H is replaced with:

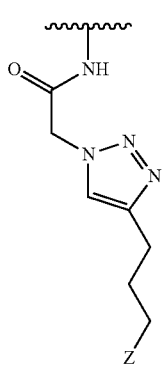

wherein Z is a halo or a radionuclide.

In another embodiment, the invention is a compound of Formula (II), wherein each $R_7$ is $CH_2C(O)NH$.

In another embodiment, the invention is a compound of Formula (II), wherein $R_8$ is aryl.

In another embodiment, the invention is a compound of Formula (II), wherein at least one H of aryl is replaced with $C_{1-8}$alkyl-halo, wherein at least one C of $C_{1-8}$alkyl-halo is optionally replaced with heteroaryl.

In another embodiment, the invention is a compound of Formula (II), that is:

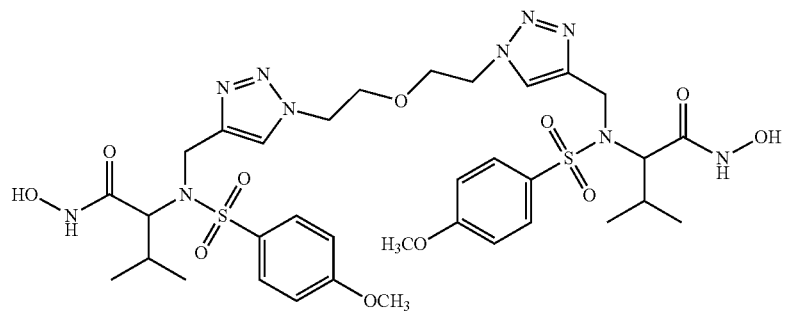 [SMILES: COc1ccc(S(=O)(=O)N(Cc2cn(CCOCCn3cc(CN(C(C(=O)NO)C(C)C)S(=O)(=O)c4ccc(OC)cc4)nn3)nn2)C(C(=O)NO)C(C)C)cc1]

and pharmaceutically acceptable salts and stereoisomers thereof.

In another embodiment, the invention is a compound of Formula (II) that is:

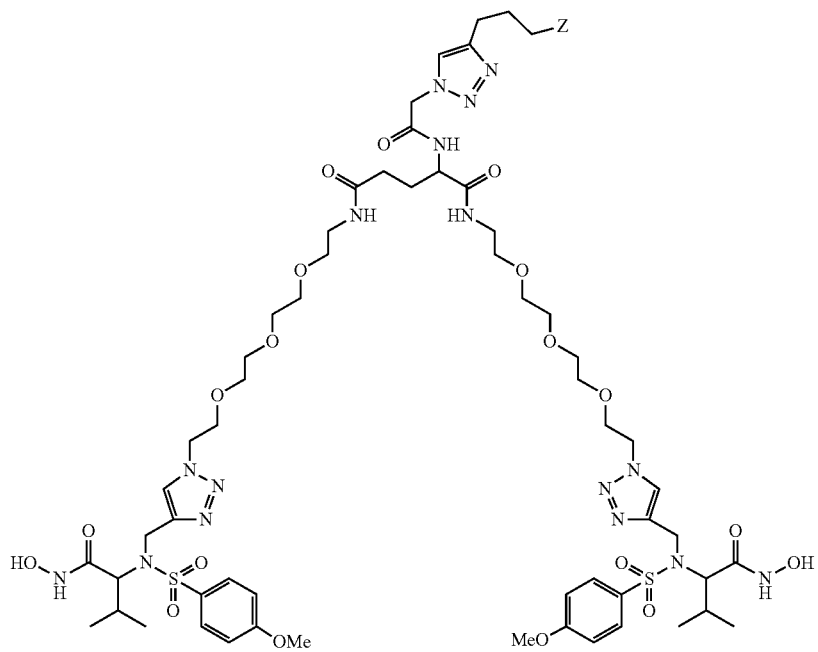

and pharmaceutically acceptable salts and stereoisomers thereof,
wherein Z is a halo or a radionuclide.

In another embodiment, the invention is a compound of Formula (II) that is:

R₃ is selected from the group consisting of: OH, NH₂, protecting group or leaving group;

R₁₀ is selected from the group consisting of: an alkyne, an azide, $C_1$-$C_6$-alkyne, $C_1$-$C_6$-azide, wherein at least one C is optionally replaced by NH, C(O), S or O,

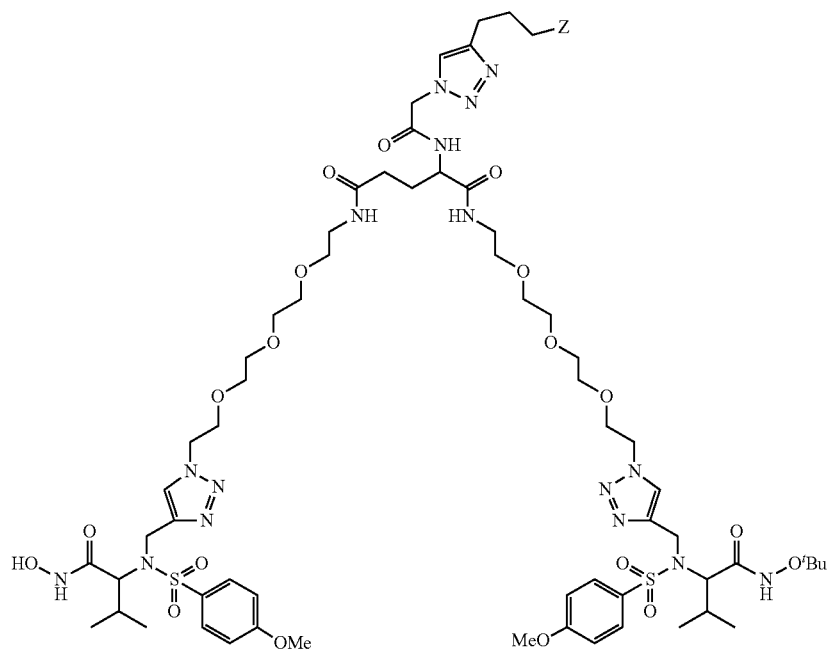

and pharmaceutically acceptable salts and stereoisomers thereof,
wherein Z is a halo or a radionuclide.

In another embodiment, the invention is a compound of Formula (III):

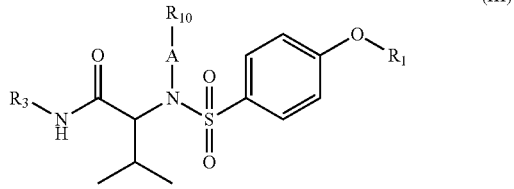

and pharmaceutically acceptable salts and stereoisomers thereof,
wherein:
$R_1$ is selected from the group consisting of: $C_{1-6}$alkyl, $C_{1-6}$alkyl-halo, protecting group or leaving group;
A is a bond, $(CH_2)_{1-5}$, or is $(-CH_2-CH_2-O-)_{1-5}$;

wherein at least one H or halo is optionally replaced with a radionuclide or a fluorophore.

In another embodiment, the invention is a compound of Formula (IV):

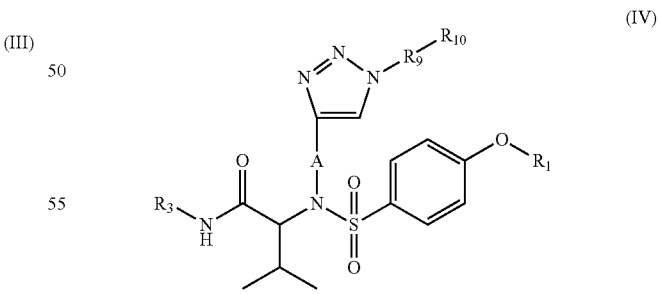

and pharmaceutically acceptable salts and stereoisomers thereof,
wherein:
$R_1$ is selected from the group consisting of: $C_{1-6}$alkyl, $C_{1-6}$alkyl-halo, protecting group or leaving group;
A is a bond, $(CH_2)_{1-5}$, or is $(-CH_2-CH_2-O-)_{1-5}$;

$R_3$ is selected from the group consisting of: OH, NH$_2$, protecting group or leaving group;

$R_9$ is a bond or is at least one selected from the group consisting of: aryl, heteroaryl, $C_{1-20}$alkyl, wherein at least one C of $C_{1-20}$alkyl is optionally replaced by O, S, NH, C(O), aryl or heteroaryl and wherein at least one H of $C_{1-20}$alkyl is optionally replaced with OH, NH$_2$, COOH, wherein at least one C of $C_{1-8}$alkyl is optionally replaced by O, S, C(O), aryl, heteroaryl or NH, $R_{10}$ is selected from the group consisting of: an alkyne, an azide, $C_1$-$C_6$-alkyne, $C_1$-$C_6$-azide, wherein at least one C is optionally replaced by NH, C(O), S or O, wherein at least one H or halo is optionally replaced with a radionuclide or a fluorophore.

In another embodiment, the invention is a compound of Formula (V):

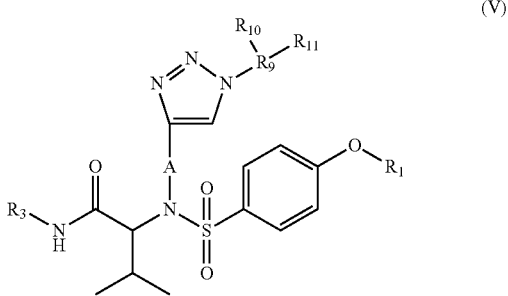

and pharmaceutically acceptable salts and stereoisomers thereof, wherein:

$R_1$ is selected from the group consisting of: $C_{1-6}$alkyl, $C_{1-6}$alkyl-halo, protecting group or leaving group;

A is a bond, $(CH_2)_{1-5}$, or is $(-CH_2-CH_2-O-)_{1-5}$;

$R_3$ is selected from the group consisting of: OH, NH$_2$, protecting group or leaving group;

$R_9$ is a bond or is at least one selected from the group consisting of: aryl, heteroaryl, $C_{1-20}$alkyl, wherein at least one C of $C_{1-20}$alkyl is optionally replaced by O, S, NH, C(O), aryl or heteroaryl and wherein one H of $C_{1-20}$alkyl is optionally replaced with OH, NH$_2$, COOH, $C_{1-8}$alkyl, $C_{1-8}$alkyl-halo, wherein at least one C of $C_{1-8}$alkyl is optionally replaced by O, S, C(O), aryl, heteroaryl or NH, $R_{10}$ is selected from the group consisting of: an alkyne, an azide, $C_1$-$C_6$-alkyne, $C_1$-$C_6$-azide, wherein at least one C of $C_1$-$C_6$ is optionally replaced by NH, C(O), S or O;

$R_{11}$ is selected from the group consisting of: H, CH$_3$, NH$_2$, OH, SO$_2$, NO$_2$, —O—$C_{1-6}$alkyl and

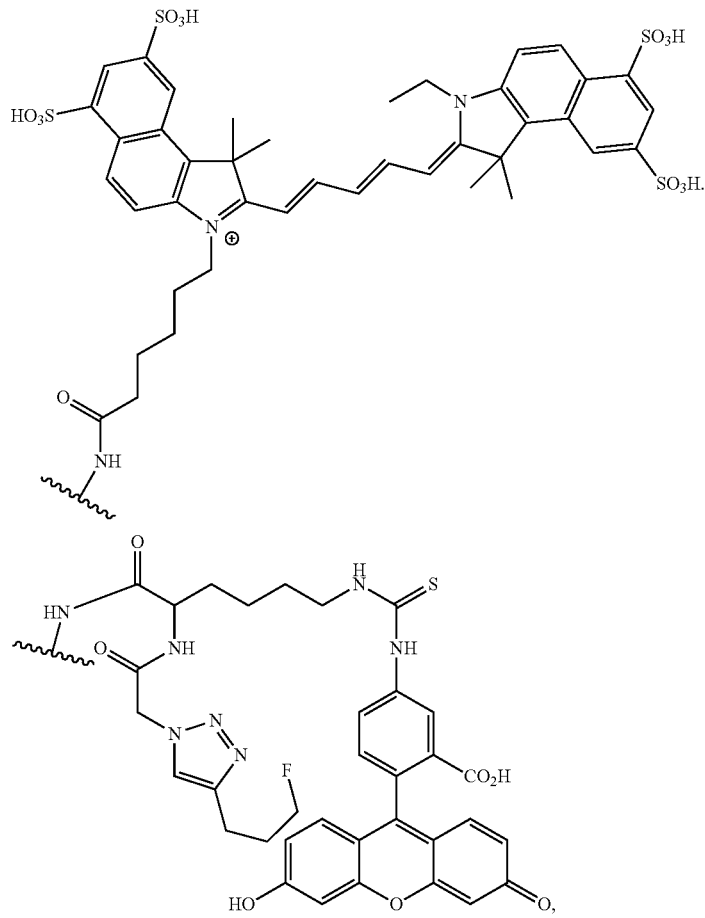

-continued

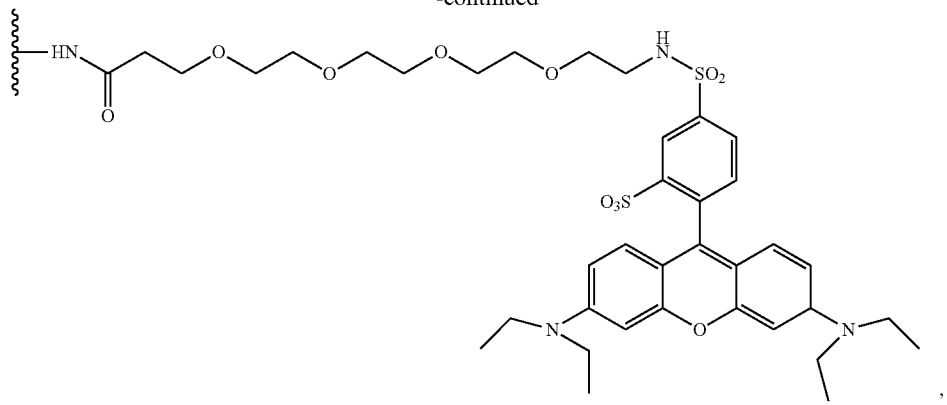
, $C_{1-20}$alkyl, $C_{1-20}$alkyl-aryl, $C_{1-20}$alkyl-heteroaryl,
wherein at least one C of the $C_{1-20}$alkyl is optionally replaced with S, $SO_2$, C(O), C(S), aryl, heteroaryl or NH,
wherein at least one H of the $C_{1-20}$alkyl, aryl or heteroaryl is replaced with halo, OH, COOH, $SO_3$, $NH_3$, N(alkyl)$_2$, $C_{1-8}$alkyl, $C_{1-8}$alkyl-halo,
wherein at least one C of $C_{1-8}$alkyl is optionally replaced by O, S, C(O), aryl, heteroaryl or NH,
wherein at least one H or halo is optionally replaced with a radionuclide or a fluorophore.

In another embodiment, the invention is a compound of Formula (VI):

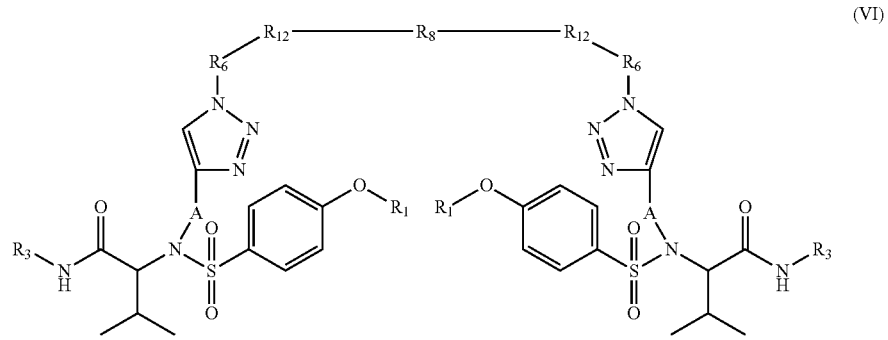

and pharmaceutically acceptable salts and stereoisomers thereof,
wherein:
each $R_1$ is independently selected from the group consisting of: $C_{1-6}$alkyl, $C_{1-6}$alkyl-halo, protecting group or leaving group;
each A is a bond, $(CH_2)_{1-5}$, or is ($-CH_2-CH_2-O-$)$_{1-5}$;
each $R_3$ is independently selected from the group consisting of: OH, $NH_2$, protecting group or leaving group;
each $R_6$ is independently a bond or is at least one selected from the group consisting of: aryl, heteroaryl, or $C_{1-20}$alkyl, wherein at least one C of $C_{1-20}$alkyl is optionally replaced by O, S, NH, C(O), aryl or heteroaryl and wherein at least one H of $C_{1-20}$alkyl is optionally replaced with OH, $NH_2$, $C_{1-8}$alkyl, $C_{1-8}$alkyl-halo,
wherein at least one C of $C_{1-8}$alkyl is optionally replaced with at least one of O, S, C(O), NH, aryl and heteroaryl;
each $R_{12}$ is independently a bond or is $C_{1-6}$alkyl, wherein at least one C of $C_{1-6}$alkyl is optionally replaced by O, S, NH, C(O) and wherein at least one H of $C_{1-6}$alkyl is optionally replaced by OH, $NH_2$, $SO_2$, $C_{1-8}$alkyl, $C_{1-8}$alkyl-halo, azide or alkyne,
wherein at least one C of $C_{1-8}$alkyl is optionally replaced by O, S, C(O), aryl, heteroaryl or NH,
$R_8$ is a bond or is at least one selected from the group consisting of: O, NH, S, aryl, heteroaryl, wherein at least one H of aryl or heteroaryl is optionally replaced with $C_{1-8}$alkyl, $C_{1-8}$alkyl-halo,
wherein at least one C of $C_{1-8}$alkyl is optionally replaced with at least one of O, S, C(O), NH, aryl and heteroaryl;
$(CH_2)_{1-6}$, wherein at least one C of $(CH_2)_{1-6}$ is optionally replaced by O, NH or S,
wherein at least one H or halo is optionally replaced with a radionuclide or a fluorophore.

In another embodiment, the invention is a compound of Formula (VII):

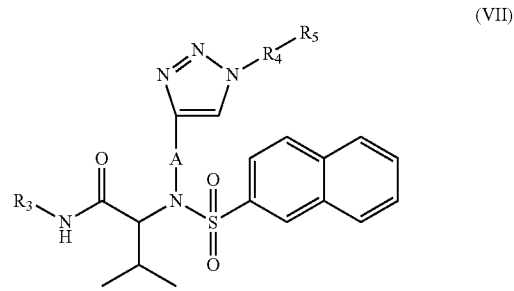

and pharmaceutically acceptable salts and stereoisomers thereof,
wherein:
A is a bond, $(CH_2)_{1-5}$, or is ($-CH_2-CH_2-O-$)$_{1-5}$;

$R_3$ is selected from the group consisting of: OH, $NH_2$, protecting group or leaving group;

$R_4$ is a bond or is at least one selected from the group consisting of: aryl, heteroaryl, $C_{1-20}$alkyl, wherein at least one C of $C_{1-20}$alkyl is optionally replaced by O, S, NH, C(O), aryl or heteroaryl and wherein at least one H of $C_{1-20}$alkyl is optionally replaced with OH, $NH_2$, COOH, $C_{1-8}$alkyl, $C_{1-8}$alkyl-halo, wherein at least one C of $C_{1-8}$alkyl is optionally replaced by O, S, C(O), aryl, heteroaryl or NH, $R_5$ is selected from the group consisting of: H, halo, $CH_3$, $NH_2$, OH, $SO_2$, $NO_2$, —O—$C_{1-6}$alkyl and $C_{1-20}$alkyl, $C_{1-20}$alkyl-aryl, $C_{1-20}$alkyl-heteroaryl, wherein at least one C of the $C_{1-20}$alkyl is optionally replaced with S, $SO_2$, C(O), C(S), aryl, heteroaryl or NH, wherein at least one H of the $C_{1-20}$alkyl, aryl or heteroaryl is replaced with halo, OH, COOH, $SO_3$, $NH_3$, $N(alkyl)_2$, $C_{1-8}$alkyl, $C_{1-8}$alkyl-halo, wherein at least one C of $C_{1-8}$alkyl is optionally replaced by O, S, C(O), aryl, heteroaryl or NH, wherein at least one H or halo is optionally replaced with a radionuclide or a fluorophore.

In another embodiment, the invention is a compound of Formula (VIII):

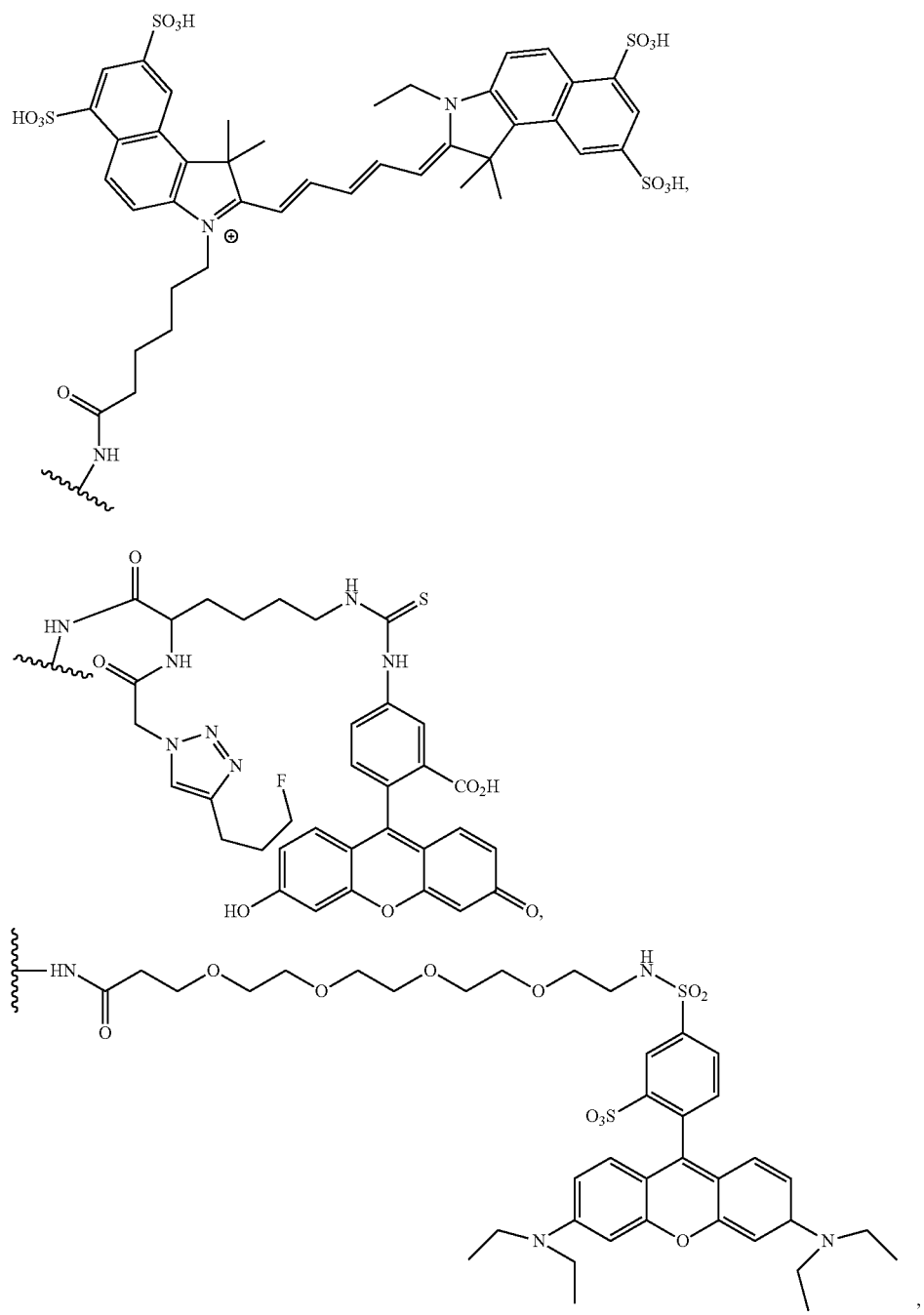

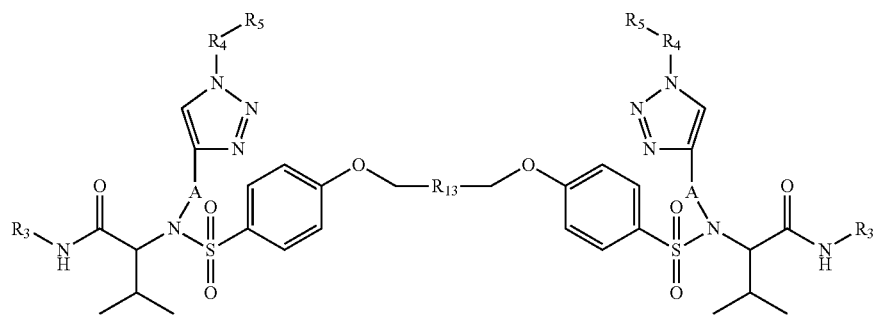

(VIII)

and pharmaceutically acceptable salts and stereoisomers thereof,
wherein:
each A is a bond, $(CH_2)_{1-5}$, or is $(-CH_2-CH_2-O-)_{1-5}$;
each $R_3$ is selected from the group consisting of: OH, $NH_2$, protecting group or leaving group;
each $R_4$ is independently a bond or is at least one selected from the group consisting of: aryl, heteroaryl, $C_{1-20}$alkyl, wherein at least one C of $C_{1-20}$alkyl is optionally replaced by O, S, NH, C(O), aryl or heteroaryl and wherein at least one H of $C_{1-20}$alkyl is optionally replaced with OH, $NH_2$, COOH, $C_{1-8}$alkyl, $C_{1-8}$alkyl-halo,
wherein at least one C of $C_{1-8}$alkyl is optionally replaced by O, S, C(O), aryl, heteroaryl or NH,
each $R_5$ is selected from the group consisting of: H, halo, $CH_3$, $NH_2$, OH, $SO_2$, $NO_2$, $-O-C_{1-6}$alkyl,

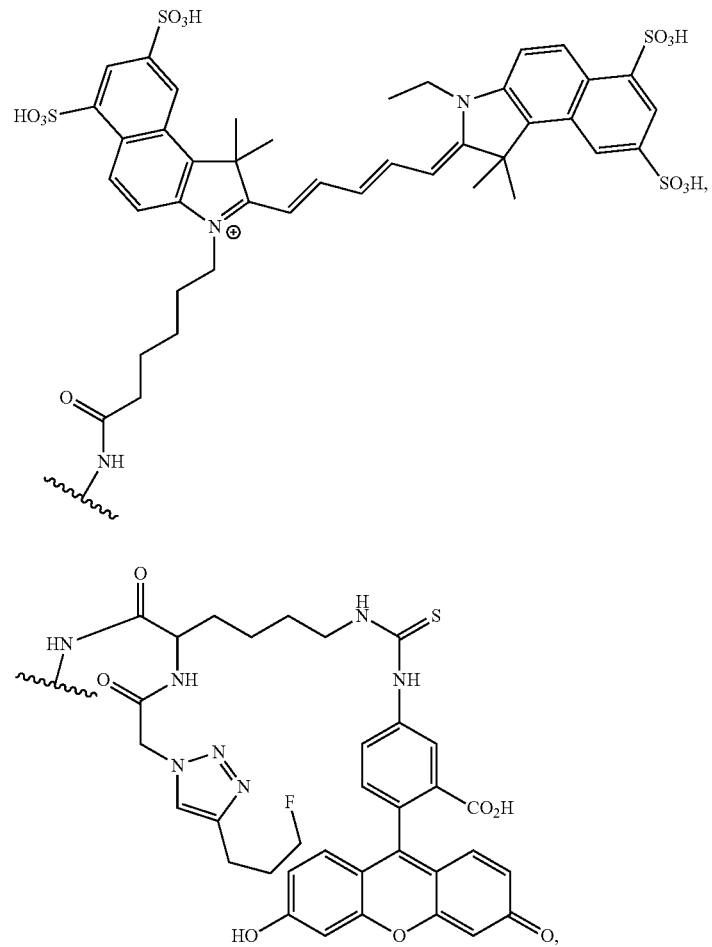

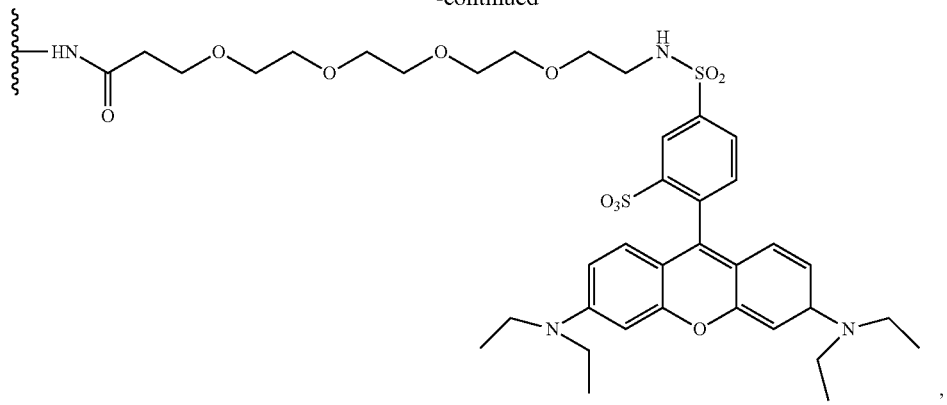

, $C_{1-20}$alkyl, $C_{1-20}$alkyl-aryl, $C_{1-20}$alkyl-heteroaryl, wherein at least one C of the $C_{1-20}$alkyl is optionally replaced with S, $SO_2$, C(O), C(S), aryl, heteroaryl or NH, wherein at least one H of the $C_{1-20}$alkyl, aryl or heteroaryl is replaced with halo, OH, COOH, $SO_3$, $NH_3$, $N(alkyl)_2$, $C_{1-8}$alkyl, $C_{1-8}$alkyl-halo, wherein at least one C of $C_{1-8}$alkyl is optionally replaced by O, S, C(O), aryl, heteroaryl or NH, $R_{13}$ is a bond or is $C_{1-20}$alkyl, wherein at least one C of the $C_{1-20}$alkyl is optionally replaced with S, $SO_2$, C(O), C(S), aryl, heteroaryl or NH, wherein at least one H or halo is optionally replaced with a radionuclide or a fluorophore.

In another embodiment, the invention is a compound of Formula (IX):

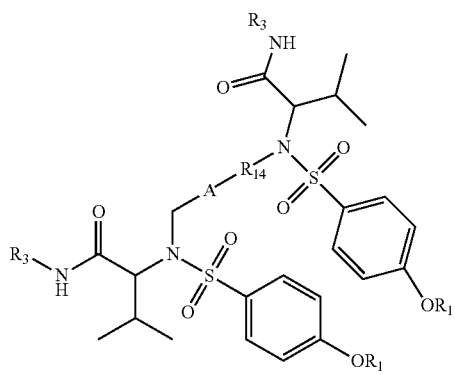

(IX)

and pharmaceutically acceptable salts and stereoisomers thereof, wherein:

each $R_1$ is independently selected from the group consisting of: $C_{1-6}$alkyl, $C_{1-6}$alkyl-halo, protecting group or leaving group;

A is a bond, $(CH_2)_{1-5}$, or is $(-CH_2-CH_2-O-)_{1-5}$;

each $R_3$ is independently selected from the group consisting of: OH, $NH_2$, protecting group or leaving group;

$R_{14}$ is independently a bond or is at least one selected from the group consisting of: aryl, heteroaryl, or $C_{1-8}$alkyl, wherein at least one C of $C_{1-8}$alkyl is optionally replaced by O, S, NH, C(O), aryl or heteroaryl, wherein at least one H or halo is optionally replaced with a radionuclide or a fluorophore.

In another embodiment, the invention is a compound of Formula (X):

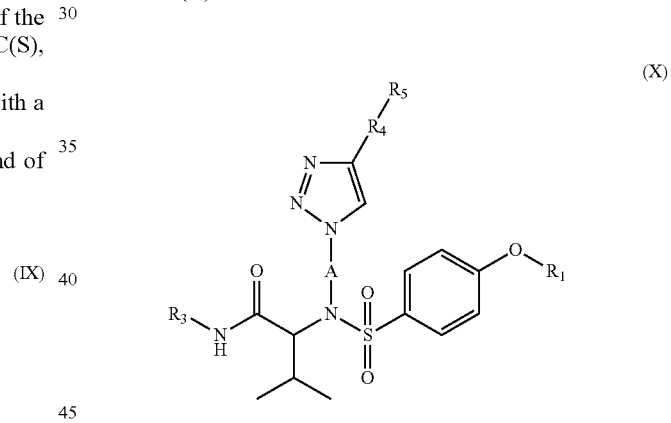

(X)

and pharmaceutically acceptable salts and stereoisomers thereof, wherein:

$R_1$ is selected from the group consisting of: $C_{1-6}$alkyl, $C_{1-6}$alkyl-halo, protecting group or leaving group;

A is a bond, $(CH_2)_{1-5}$, or is $(-CH_2-CH_2-O-)_{1-5}$;

$R_3$ is selected from the group consisting of: OH, $NH_2$, protecting group or leaving group;

$R_4$ is a bond or is at least one selected from the group consisting of: aryl, heteroaryl, $C_{1-20}$alkyl, wherein at least one C of $C_{1-20}$alkyl is optionally replaced by O, S, NH, C(O), aryl or heteroaryl and wherein at least one H of $C_{1-20}$alkyl is optionally replaced with OH, $NH_2$, COOH, wherein at least one C of $C_{1-8}$alkyl is optionally replaced by O, S, C(O), aryl, heteroaryl or NH, $R_5$ is selected from the group consisting of: H, halo, $CH_3$, $NH_2$, OH, $SO_2$, $NO_2$, $-O-C_{1-6}$alkyl,

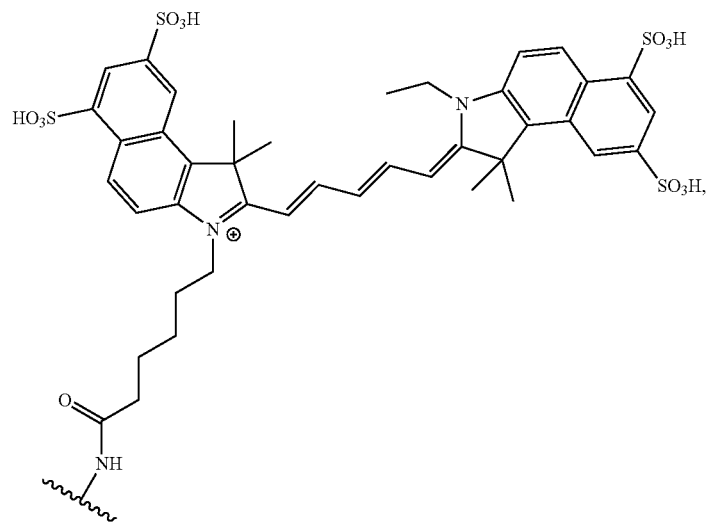
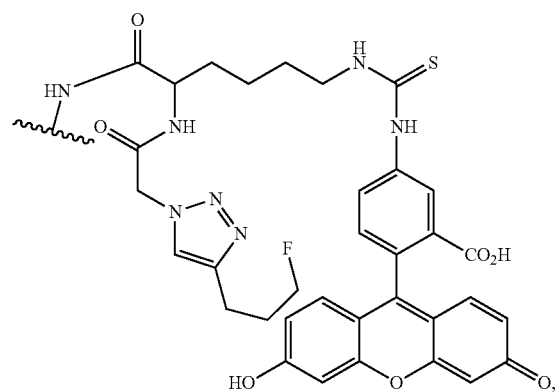
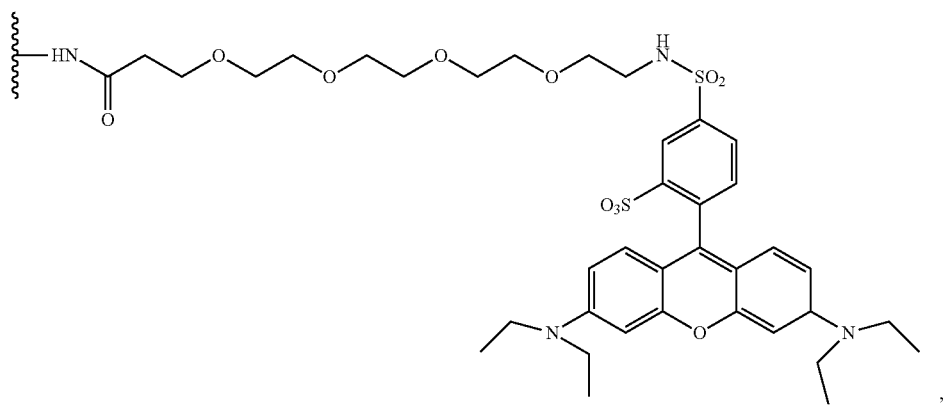

$C_{1-20}$alkyl, $C_{1-20}$alkyl-aryl, $C_{1-20}$alkyl-heteroaryl, wherein at least one C of the $C_{1-20}$alkyl is optionally replaced with S, $SO_2$, C(O), C(S), aryl, heteroaryl or NH, wherein at least one H of the $C_{1-20}$alkyl, aryl or heteroaryl is replaced with halo, OH, COOH, $SO_3$, $NH_3$, $N(alkyl)_2$, $C_{1-8}$alkyl, $C_{1-8}$alkyl-halo, wherein at least one C of $C_{1-8}$alkyl is optionally replaced by O, S, C(O), aryl, heteroaryl or NH, wherein at least one H or halo is optionally replaced with a radionuclide or a fluorophore.

In another embodiment, the invention is a compound of Formula (X) that is:

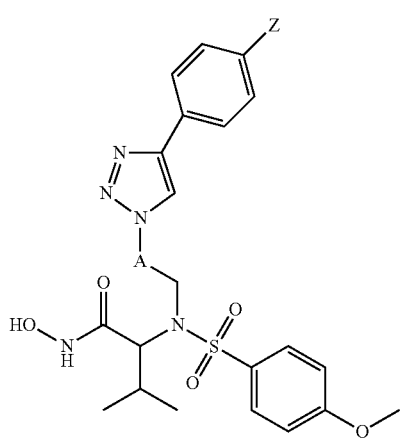

wherein Z is selected from the group consisting of: $NH_2$, OMe, halo or radionuclide.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. A variety of modifications to the embodiments described will be apparent to those skilled in the art from the disclosure provided herein. Thus, the present invention may be embodied in other specific forms without departing from the spirit or essential attributes thereof. Various changes may be made without departing from the spirit and scope of the inventions as defined in the following claims.

We claim:

1. A pharmaceutically acceptable salt of:

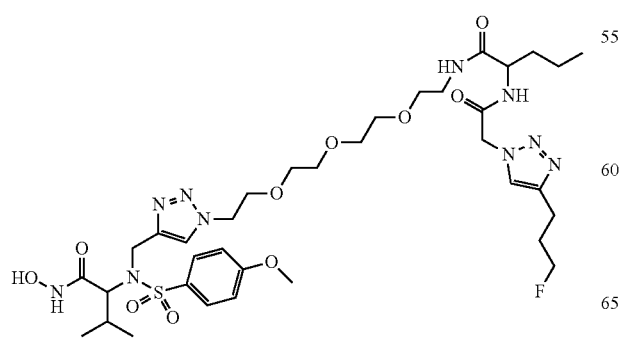

-continued

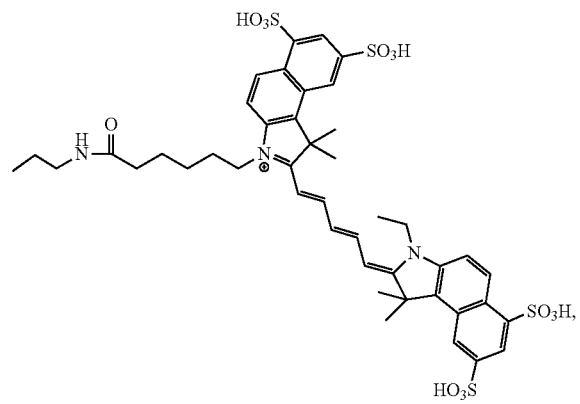

or a stereoisomer thereof.

2. A compound that is:

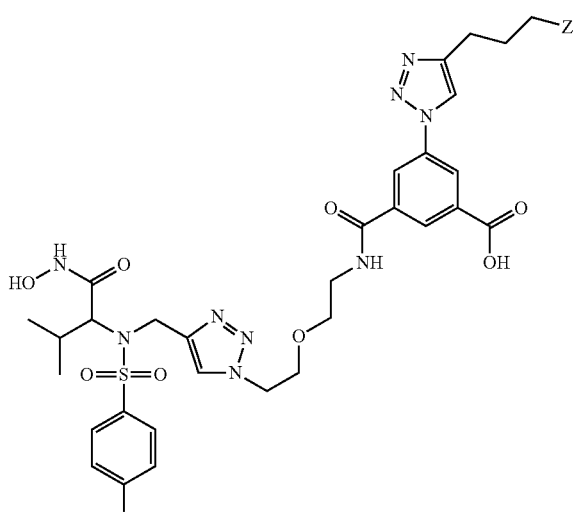

or a pharmaceutically acceptable salt or stereoisomer thereof, wherein Z is a halo or a radionuclide.

3. A compound that is:
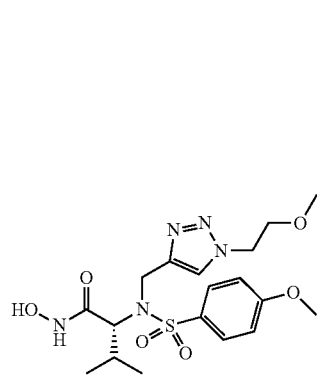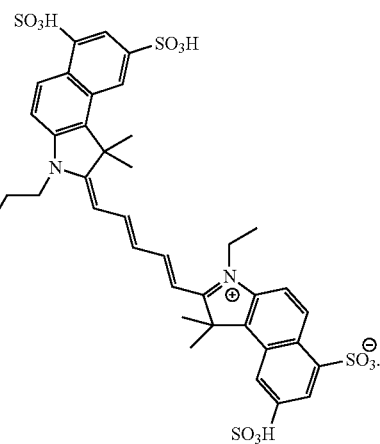
or a pharmaceutically acceptable salt or stereoisomer thereof.
4. A pharmaceutically acceptable salt of Formula (IA):

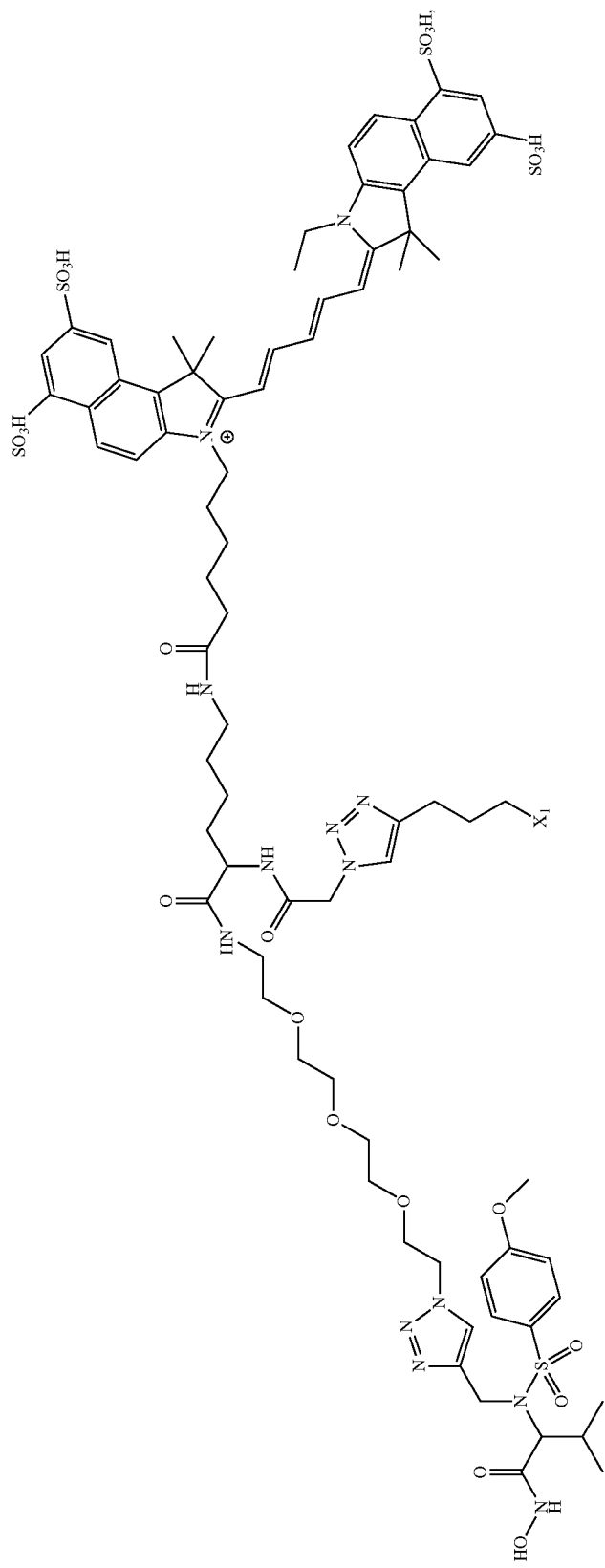

or a stereoisomer thereof;
wherein $X_1$ is selected from the group consisting of halo, fluorophore or radioactive halo.

5. The compound of claim 4, wherein $X_1$ is F.

6. The compound of claim 4, wherein $X_1$ is $^{18}$F.

* * * * *